US011077236B2

(12) United States Patent
Doerr et al.

(10) Patent No.: US 11,077,236 B2
(45) Date of Patent: Aug. 3, 2021

(54) POWERED LAVAGE HANDLE AND ASSOCIATED USE THEREFORE

(71) Applicants: Daniel Glenn Doerr, Orlando, FL (US); Roland Strelitzki, Altamonte Springs, FL (US); Mohammed Ali Barakat, Casselberry, FL (US); Keith Anderson, Orlando, FL (US); Gary Wayne Haberland, Winter Park, FL (US); John A. Farnella, Orlando, FL (US); Kenneth M. Roger, Casselberry, FL (US)

(72) Inventors: Daniel Glenn Doerr, Orlando, FL (US); Roland Strelitzki, Altamonte Springs, FL (US); Mohammed Ali Barakat, Casselberry, FL (US); Keith Anderson, Orlando, FL (US); Gary Wayne Haberland, Winter Park, FL (US); John A. Farnella, Orlando, FL (US); Kenneth M. Roger, Casselberry, FL (US)

(73) Assignee: GENICON, INC., Winter Park, FL (US)

( * ) Notice: Subject to any disclaimer, the term of this patent is extended or adjusted under 35 U.S.C. 154(b) by 0 days.

(21) Appl. No.: 14/890,528

(22) PCT Filed: Nov. 9, 2015

(86) PCT No.: PCT/US2015/059780
§ 371 (c)(1),
(2) Date: Nov. 11, 2015

(87) PCT Pub. No.: WO2016/099709
PCT Pub. Date: Jun. 23, 2016

(65) Prior Publication Data
US 2017/0119939 A1     May 4, 2017

Related U.S. Application Data

(60) Provisional application No. 62/092,112, filed on Dec. 15, 2014.

(51) Int. Cl.
*A61M 1/00* (2006.01)
*A61M 3/02* (2006.01)

(52) U.S. Cl.
CPC ........ *A61M 1/0064* (2013.01); *A61M 1/0035* (2014.02); *A61M 3/0283* (2013.01)

(58) Field of Classification Search
CPC . A61M 1/0064; A61M 3/0283; A61M 1/0035
See application file for complete search history.

(56) References Cited

U.S. PATENT DOCUMENTS

| 3,353,537 A | 11/1967 | Knox et al. |
| 3,889,675 A | 6/1975 | Stewart |
| (Continued) | | |

OTHER PUBLICATIONS

Striker, Disposable Pump Product, Strykeflow II Disp. Suction/Irr (Website) https://www.stryker.com/en-us/products/Endoscopy/Laparoscopy/SuctionIrrigation/StrykeFlow2/index.htm.
(Continued)

*Primary Examiner* — Amber R Stiles
(74) *Attorney, Agent, or Firm* — Nixon Peabody LLP; Jeffrey L. Costellia

(57) ABSTRACT

A lavage handle for facilitating at least one of an irrigation function and a suctioning function at a target zone preferably includes a portable body, a power-operated fluid-displacing mechanism in communication with said body wherein said fluid-displacing mechanism has one of a first operating mode for inducing outward irrigation of fluid towards the target zone and a second operating mode for inducing inward suction of fluid from the target zone. An actuation mechanism is located at said body and operable communi-
(Continued)

cated with said fluid-displacing mechanism such that said fluid-displacing mechanism is selectively operated in at least one of said first operating mode and said second operating mode. The actuation mechanism may include an irrigation-inducing mechanism and/or a suction-inducing mechanism.

25 Claims, 21 Drawing Sheets

(56) References Cited

U.S. PATENT DOCUMENTS

| | | | |
|---|---|---|---|
| 4,282,867 A | 8/1981 | Du Toit | |
| 4,508,532 A | 4/1985 | Drews et al. | |
| 4,583,531 A | 4/1986 | Mattchen | |
| 4,705,500 A | 11/1987 | Reunels et al. | |
| 4,776,840 A | 10/1988 | Freitas et al. | |
| 4,817,599 A | 4/1989 | Drews | |
| 4,832,685 A | 5/1989 | Haines | |
| 5,046,486 A | 9/1991 | Grulke et al. | |
| 5,197,458 A | 3/1993 | Ito et al. | |
| 5,716,007 A | 2/1998 | Nottingham et al. | |
| 5,882,319 A | 3/1999 | Olson et al. | |
| 5,941,851 A | 8/1999 | Coffey et al. | |
| 6,059,754 A * | 5/2000 | Pasch | A61M 3/0258 601/161 |
| 6,461,323 B2 | 10/2002 | Fowler et al. | |
| 6,623,445 B1 | 9/2003 | Nelson et al. | |
| 7,144,383 B2 | 12/2006 | Arnett et al. | |
| 2002/0002372 A1* | 1/2002 | Jahns | A61B 18/1492 606/41 |
| 2004/0138527 A1* | 7/2004 | Bonner | A61B 18/1485 600/114 |
| 2005/0159740 A1* | 7/2005 | Paul | A61B 18/1402 606/41 |
| 2008/0154183 A1* | 6/2008 | Baker | A61M 1/0058 604/28 |
| 2012/0035545 A1* | 2/2012 | Schwarz | A61M 3/0258 604/151 |
| 2013/0324917 A1* | 12/2013 | Akagane | A61B 17/320092 604/35 |
| 2014/0207056 A1* | 7/2014 | Bono | A61M 3/0283 604/34 |

OTHER PUBLICATIONS

Cardinal Intellectual Property, Patent Search, pp. 1-5.
Gyrus ACMI, Disposable Pump Product, (Website) www.gyrusacmi.com, 2008.
Stryker Instruments, InterPulse Battery Powered Irrigation (Brochure), Accessed on Oct. 2015.
Bard Davol Inc., 2015, Bard® Laparoscopic Irrigation Systems (Brochure).
Bard Davol Inc. http://www.davol.com/products/laparoscopic-irrigation/sp/hydro-surg-plus/ (Website), Accessed on Oct. 2015.
Gyrus ACMI, 2008, Surgical Product (Catalog), www.gyrusacmi.com.
Gyrus ACMI, 2008, PK.TM Technology for Laparoscopic Surgery (Catalog) www.gyrusacmi.com.
Gyrus ACMI, 2008, PK.TM Technology for Open Surgery (Catalog) www.gyrusacmi.com.
Gyrus ACMI, 2008, Everest Bipolar for Laparoscopic Surgery (Catalog) www.gyrusacmi.com.
Gyrus ACMI, 2008, Laparoscopy (Catalog) www.gyrusacmi.com.
Gyrus ACMI, Disposable Pump Product, (Website) www.gyrusacmi.com.
Zimmer, 2008, Pulsvac Plus Family (Catalog) http://www.zimmer.com/medical-professionals/products/surgical-and-operating-room-solutions/pulsavac-plus-wound-debridement.html.

* cited by examiner

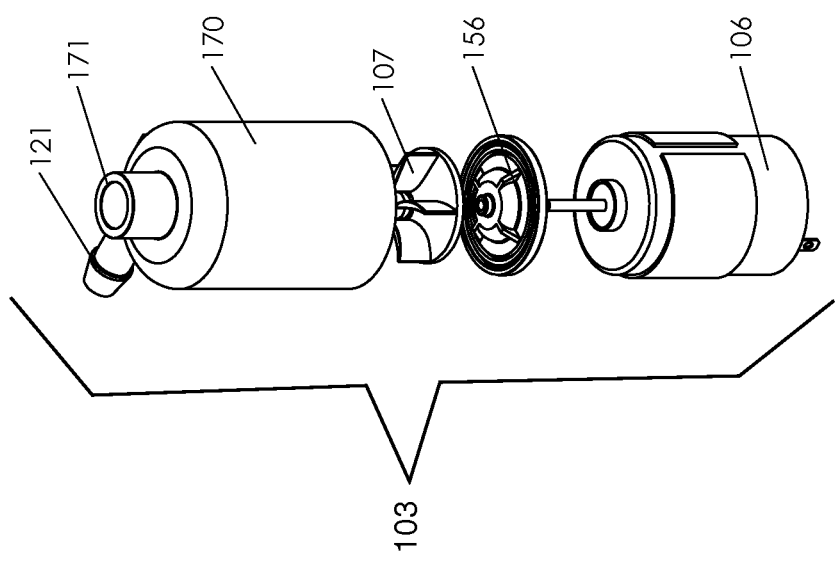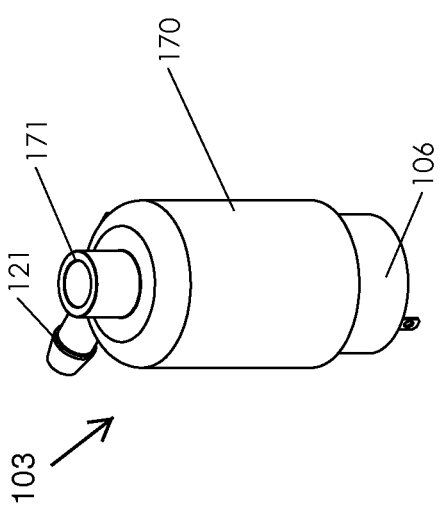
Fig. 7B
Fig. 7A

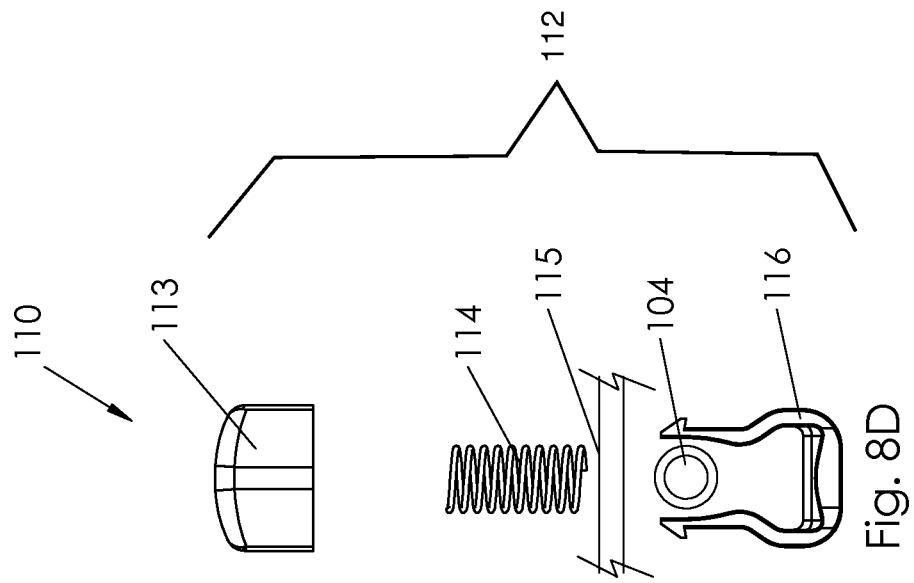
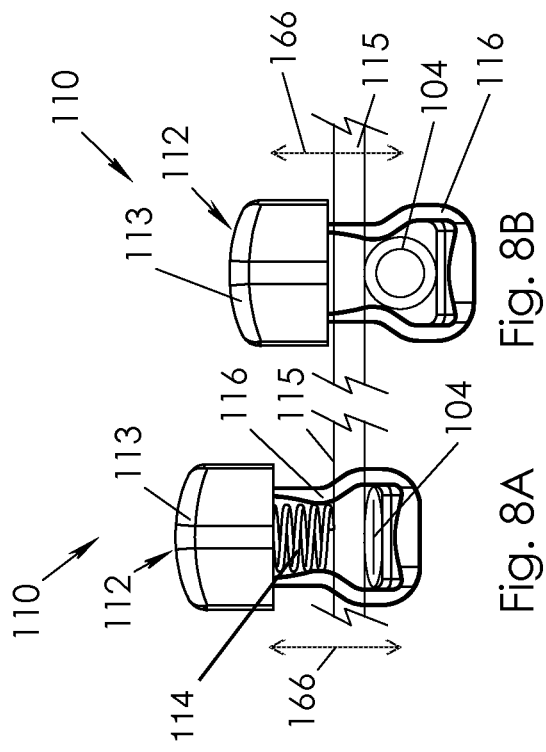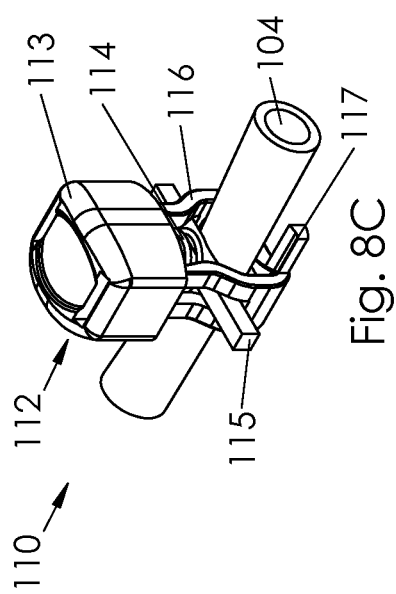

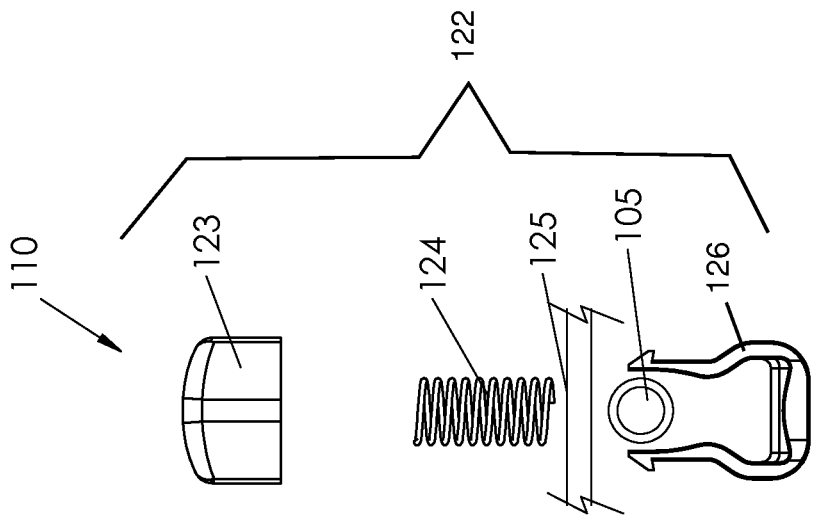
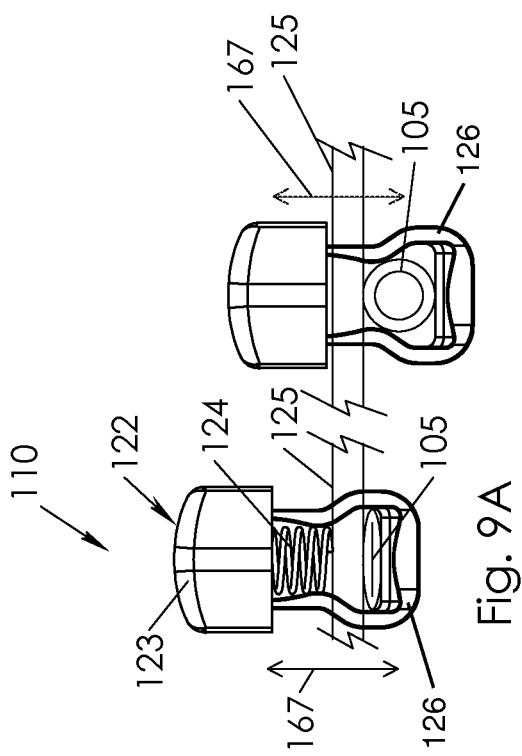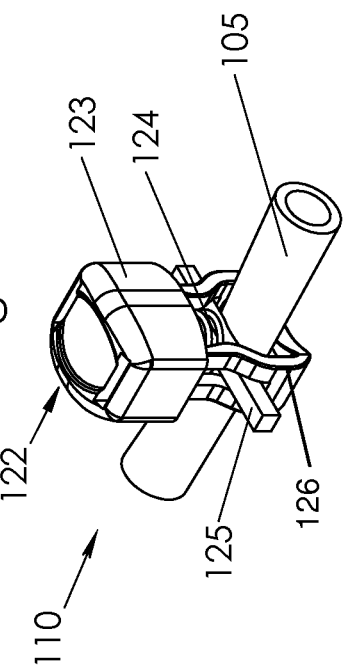

POWERED LAVAGE HANDLE AND ASSOCIATED USE THEREFORE

CROSS REFERENCE TO RELATED APPLICATIONS

This United States Non-provisional Patent Application claims priority to and the benefit of, and is a National Phase entry of currently pending International Patent Cooperation Treaty Application No. PCT/US15/59780, filed on Nov. 9, 2015, which claims priority to and the benefit of U.S. Provisional Application No. 62/092,112 filed Dec. 15, 2014, both of which are herein incorporated by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

Exemplary embodiment(s) of the present disclosure relate to lavage devices and, more particularly, to a lavage handle used to retrieve and/or discharge fluid to a target zone wherein an actuation mechanism switches a fluid-displacing mechanism between operating and non-operating modes. The fluid-displacing mechanism can be physically incorporated completely within a body of the handle. A feedback mechanism may be provided to notify the user when the fluid-displacing mechanism is operating.

Prior Art

Development of laparoscope procedures has given physicians the ability to see inside the body without the necessity of large incisions and their related hazard of infection. Use of a laparoscope, and other related devices, allows the physician to perform a variety of diagnostic and surgical procedures. The scope allows the introduction of microsurgical tools through the scope housing without impeding the physician's vision, permitting simultaneous viewing of the affected area and manipulation of the tools. During these procedures, it is often desirable to irrigate tissues. Following irrigation, or when bleeding occurs, or when smoke is generated by heat or laser evaporation of tissues, it is often necessary to apply a vacuum (e.g., suction) to evacuate the area of smoke, blood, or irrigating solution to permit continued unobstructed viewing of the area.

Among the common techniques for maintaining a clean surgical site is to irrigate the site with an irrigation or antiseptic solution. Typically, the liquid is supplied from a reservoir through tubing to a dispensing handle that is manipulated by the surgeon or a surgical assistant. Removal of the irrigation liquid as well as other fluids may collect at the surgical site is effected by applying a suction instrument in the region. A number of irrigation devices have been used and proposed. Generally, they incorporate an arrangement for developing and delivering the liquid. Among the systems employed in the prior art include one that are powered by external energy sources, including electrically and pneumatically driven pumps. Some systems employ complex peripheral controls to vary the characteristics of the emitted fluid stream. The external location of such energy sources and complexity of peripheral controls frustrates an operator's ability to freely maneuver the device both during and after the laparoscopic procedure.

Accordingly, a need remains for an improved lavage handle in order to overcome at least one prior art shortcoming mentioned hereinabove. The exemplary embodiment(s) satisfy such a need by providing a lavage handle including a fluid-displacing mechanism physically incorporated completely within a body of the handle that is convenient and easy to use, lightweight yet durable in design, versatile in its applications, and designed for retrieving and/or discharging fluid to a target zone.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a lavage handle for facilitating at least one of an irrigation function and a suctioning function at a target zone. These and other objects, features, and advantages of the non-limiting exemplary embodiment(s) are provided by a lavage handle including a body, and a fluid-displacing mechanism in communication with the body wherein the fluid-displacing mechanism has one of a first operating mode for inducing outward irrigation of fluid towards the target zone and a second operating mode for inducing inward suction of fluid from the target zone. The lavage handle further includes an actuation mechanism located at the body and operable communicated with the fluid-displacing mechanism such that the fluid-displacing mechanism is selectively operated in at least one of the first operating mode and the second operating mode.

In a non-limiting exemplary embodiment, the actuation mechanism is disposed at least partially exterior of the body.

In a non-limiting exemplary embodiment, the actuation mechanism includes a multi-pole toggle switch.

In a non-limiting exemplary embodiment, the actuation mechanism includes at least one rheostat.

In a non-limiting exemplary embodiment, the actuation mechanism includes a spring-resistive trigger.

In a non-limiting exemplary embodiment, the actuation mechanism is disposed entirely interior of the body.

In a non-limiting exemplary embodiment, the body is formed from deformably resilient material.

In a non-limiting exemplary embodiment, the actuation mechanism includes a pressure-sensitive contact in communication with the deformably resilient material such that the fluid-displacing mechanism is operated when the body is biased to a tensioned state.

In a non-limiting exemplary embodiment, the lavage handle further includes a feedback mechanism in communication with the fluid-displacing mechanism for notifying the user of at least one of the first operating mode and the second operating mode.

In a non-limiting exemplary embodiment, the feedback mechanism includes at least one transducer for generating and emitting at least one alert signal when the fluid-displacing mechanism is at one of the first operating mode and the second operating mode.

In a non-limiting exemplary embodiment, the at least one alert signal is selected from the group including: an audio signal, a visual signal, a mechanical signal, a sensory signal and a combination thereof.

In a non-limiting exemplary embodiment, the feedback mechanism is located interior of the body.

In a non-limiting exemplary embodiment, the feedback mechanism is located at least partially exterior of the body.

In a non-limiting exemplary embodiment, a lavage handle includes a portable body, and a power-operated fluid-displacing mechanism in communication with the body wherein the fluid-displacing mechanism has one of a first operating mode for inducing outward irrigation of fluid towards the target zone and a second operating mode for inducing inward suction of fluid from the target zone. Such a lavage handle further includes an actuation mechanism located at the body and operable communicated with the power-operated fluid-displacing mechanism such that the power-operated fluid-displacing mechanism is selectively operated in at least one of the first operating mode and the second operating mode.

In a non-limiting exemplary embodiment, the lavage handle further includes a user-interface, a voice-activated mechanism operatively coupled to the actuation mechanism. In this manner, upon receiving a user input signal, the user-interface generates and transmits a corresponding control signal to the voice-activated mechanism for operating the actuation mechanism.

In a non-limiting exemplary embodiment, the lavage handle further includes a flow monitoring mechanism in communication with the power-operated fluid-displacing mechanism. Such a flow monitoring mechanism monitors at least one of a flow pressure, flow rate, and a volume of the fluid passing through the body.

In a non-limiting exemplary embodiment, the lavage handle further includes an optics generating mechanism in communication with the body. Such an optics generating mechanism includes at least one of a light source for illuminating the target zone and a camera for capturing a visual image of the target zone.

In a non-limiting exemplary embodiment, the lavage handle further includes a fluid storage container in communication with the power-operated fluid-displacing mechanism. Such a fluid storage container includes at least one of an irrigation container and a suction container in communication with the body.

In a non-limiting exemplary embodiment, the first operating mode of the power-operated fluid-displacing mechanism causes fluid displacement from the irrigation container to the target zone. In this manner, the second operating mode of the power-operated fluid-displacing mechanism causes fluid retrieval from the target zone to the suction container.

In a non-limiting exemplary embodiment, the lavage handle further includes a probe connector in fluid communication with the body, and at least one of a suction probe and an irrigation probe in fluid communication with the probe connector.

In a non-limiting exemplary embodiment, the power-operated fluid-displacing mechanism is at least partially contained within the body.

In a non-limiting exemplary embodiment, the actuation mechanism includes an irrigation-inducing mechanism.

In a non-limiting exemplary embodiment, the actuation mechanism includes a suction-inducing mechanism.

The present disclosure further includes a method of utilizing a lavage handle for facilitating at least one of an irrigation function and a suctioning function at a target zone. Such a method includes the steps of: providing a portable body; providing and communicating a power-operated fluid-displacing mechanism with the body wherein the fluid-displacing mechanism has one of a first operating mode for inducing outward irrigation of fluid towards the target zone and a second operating mode for inducing inward suction of fluid from the target zone; providing and locating an actuation mechanism at the body; and operably communicating the actuation mechanism with the fluid-displacing mechanism such that the fluid-displacing mechanism is selectively operated in at least one of the first operating mode and the second operating mode.

In a non-limiting exemplary embodiment, the method further includes the steps of: accessing a surgical procedure; and employing the lavage handle during the surgical procedure.

In a non-limiting exemplary embodiment, the method further includes the steps of: accessing a surgical port; and employing the lavage handle in conjunction with the surgical port.

In a non-limiting exemplary embodiment, the method further includes the steps of: obtaining at least one of a suction probe and an irrigation probe; and employing the lavage handle in conjunction with the at least one of a suction probe and an irrigation probe.

There has thus been outlined, rather broadly, the more important features of non-limiting exemplary embodiment (s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 7A is an enlarged perspective view of the motor housing and impeller housing in communication with the irrigation port and motor;

FIG. 7B is an exploded view illustrating the interconnection between the impeller and motor housed in FIG. 7A;

FIG. 8A is an enlarged elevational view of the irrigation-inducing section wherein the irrigation button and tube clamp are released to a raised position relative to a stationary pin thereby closing (e.g., pinching, collapsing, etc.) the irrigation tube;

FIG. 8B is an enlarged elevational view of the irrigation-inducing section wherein the irrigation button and tube clamp are pressed to a lowered position relative to a stationary pin thereby opening (e.g., discharging, releasing, etc.) the irrigation tube;

FIG. 8C is a perspective view of the irrigation button and tube clamp pressed to a lowered position as illustrated in FIG. 8B;

FIG. 8D is an exploded side elevational view of the irrigation-inducing section illustrated in FIGS. 8A-8C;

FIG. 9A is an enlarged elevational view of the suction-inducing section wherein the suction button and tube clamp are released to a raised position thereby closing (e.g., pinching, collapsing, etc.) the suction tube;

FIG. 9B is an enlarged elevational view of the suction button and tube clamp pressed to a lowered position thereby opening (e.g., discharging, releasing, etc.) the suction tube;

FIG. 9C is an enlarged perspective view of the suction button and tube clamp pressed to a lowered position as illustrated in FIG. 9B;

FIG. 9D is an exploded side elevational view of the suction-inducing section illustrated in FIGS. 9A-9C;

Figure 1:
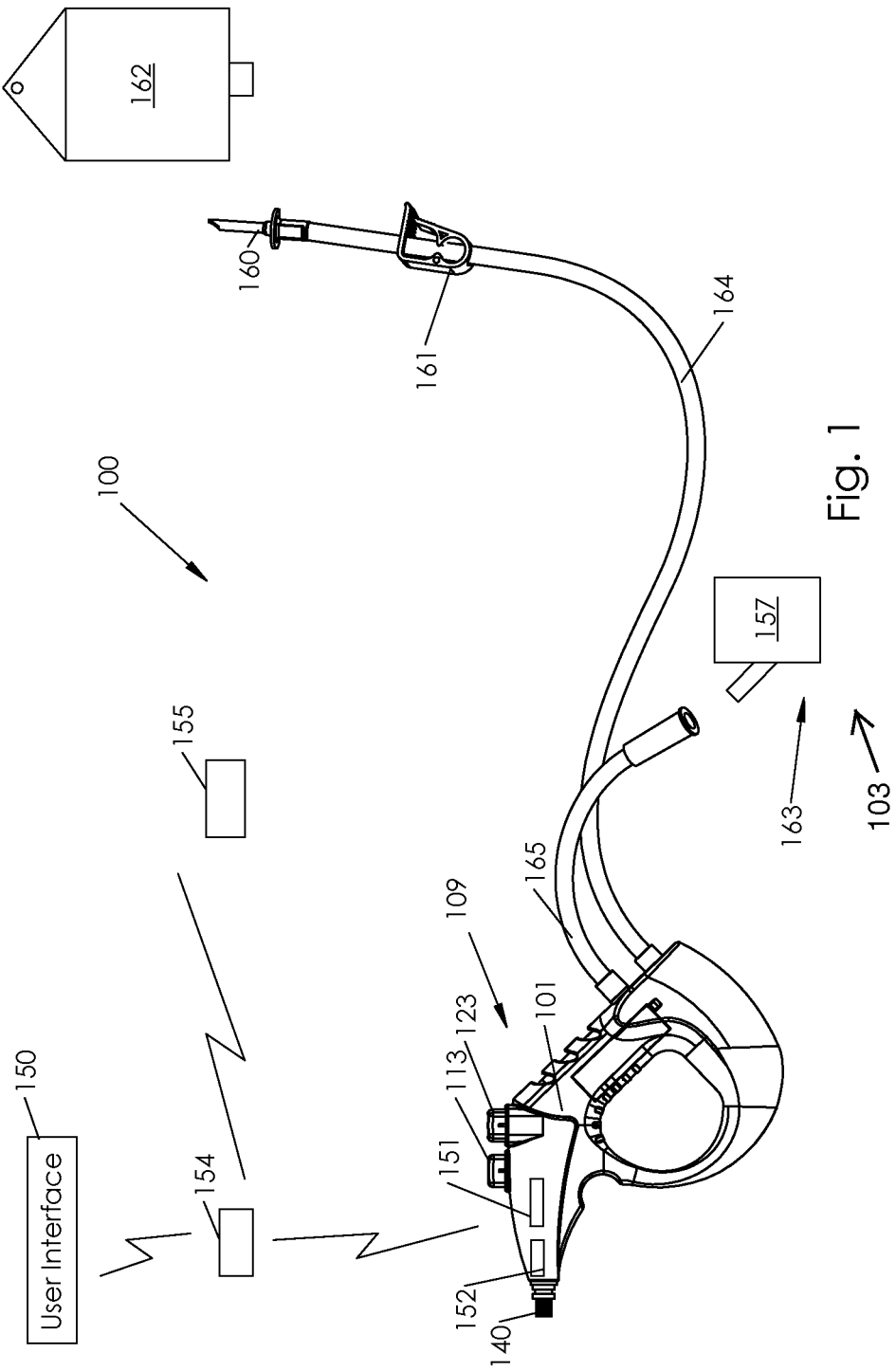
FIG. 1 is a schematic diagram illustrating a lavage handle in communication with peripheral components associated therewith, in accordance with a non-limiting exemplary embodiment of the present disclosure.
Figure 2:
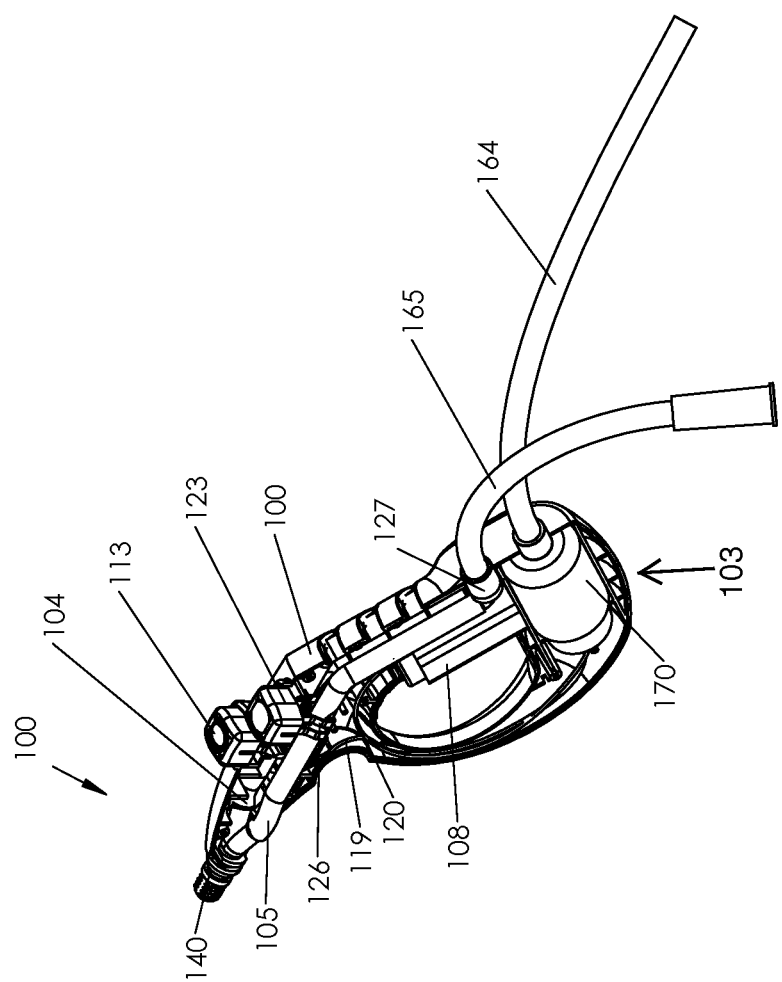
FIG. 2 is an enlarged perspective view of the lavage handle illustrated in FIG. 1, wherein a suction side of the handle is exposed.
Figure 3:
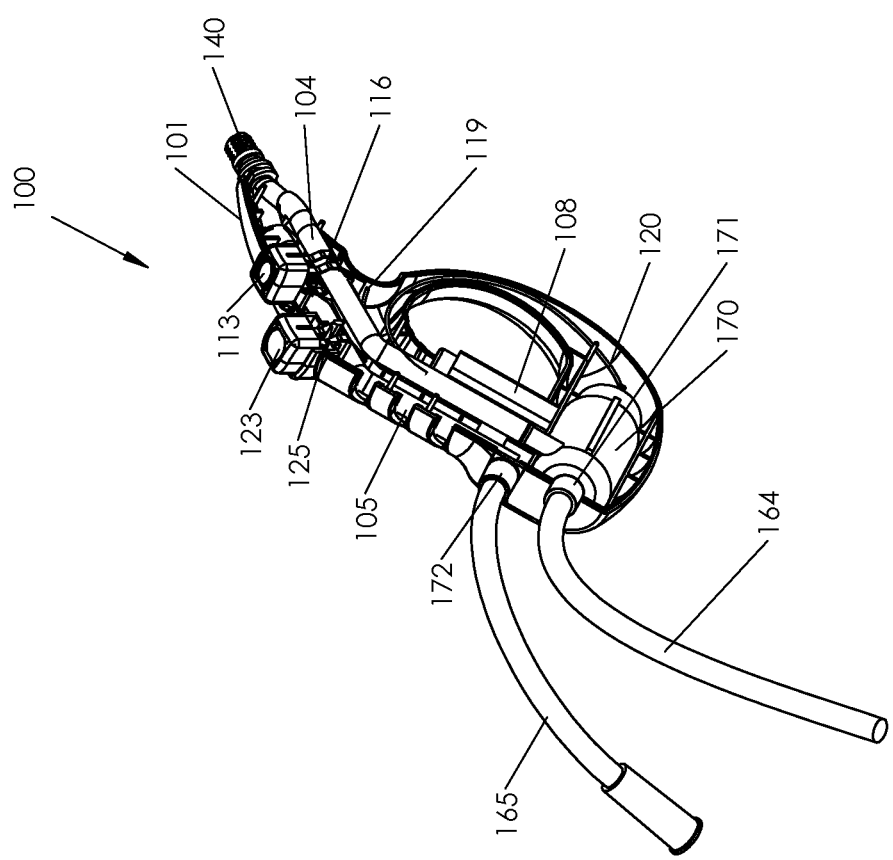
FIG. 3 is another enlarged perspective view of the lavage handle illustrated in FIG. 1, wherein an irrigation side of the handle is exposed.
Figure 4:
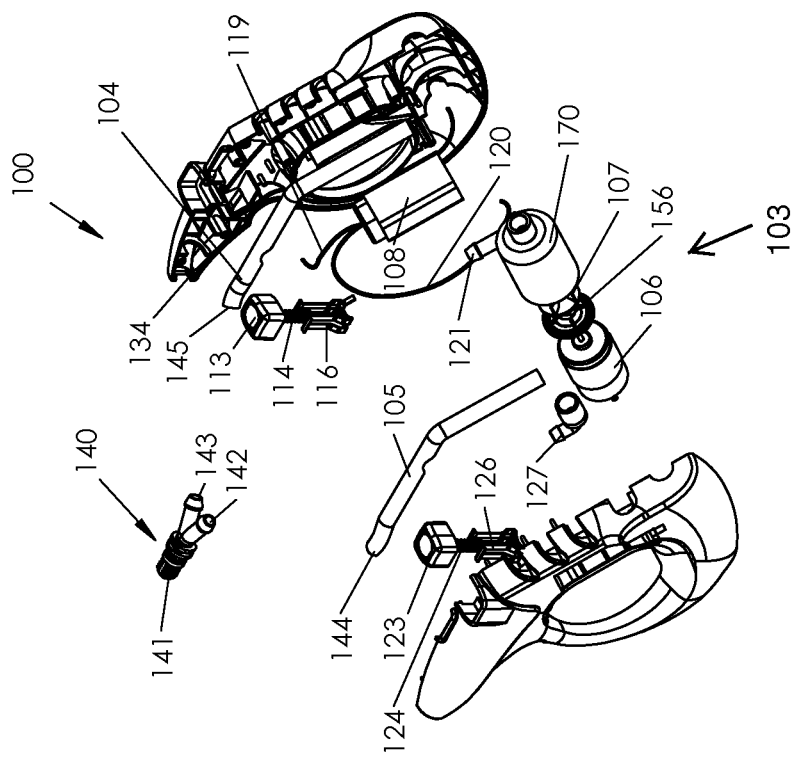
FIG. 4 is an enlarged exploded view of the lavage handle illustrated in FIG. 1.
Figure 5:
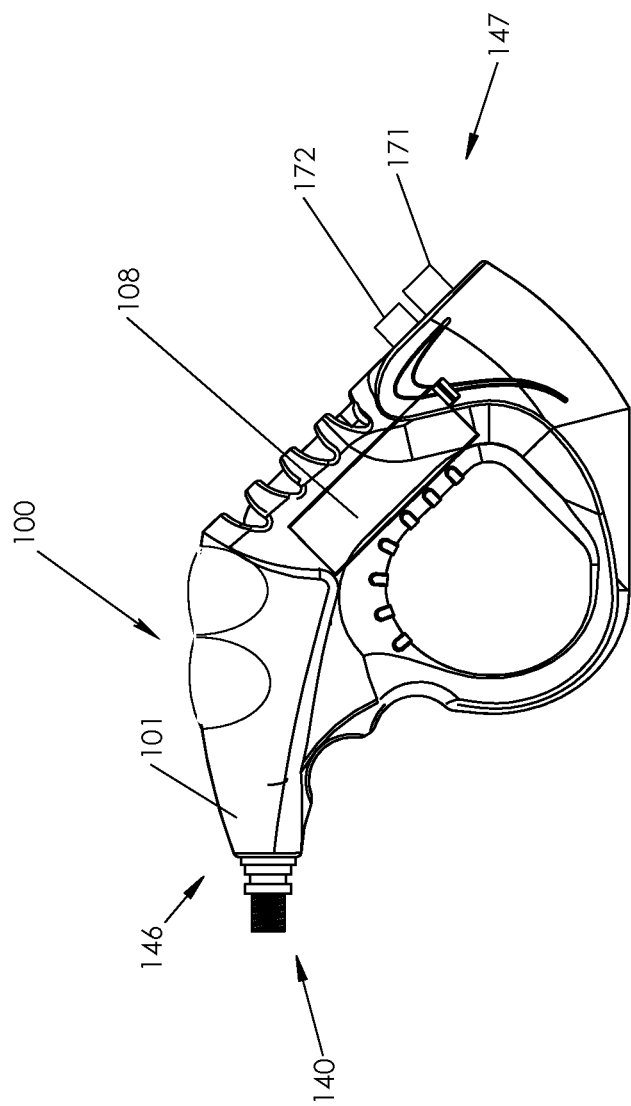
FIG. 5 is an enlarged side elevational view of the lavage handle illustrated in FIG. 1, wherein suction and irrigation buttons are removed from a top surface of the handle.
Figure 6:
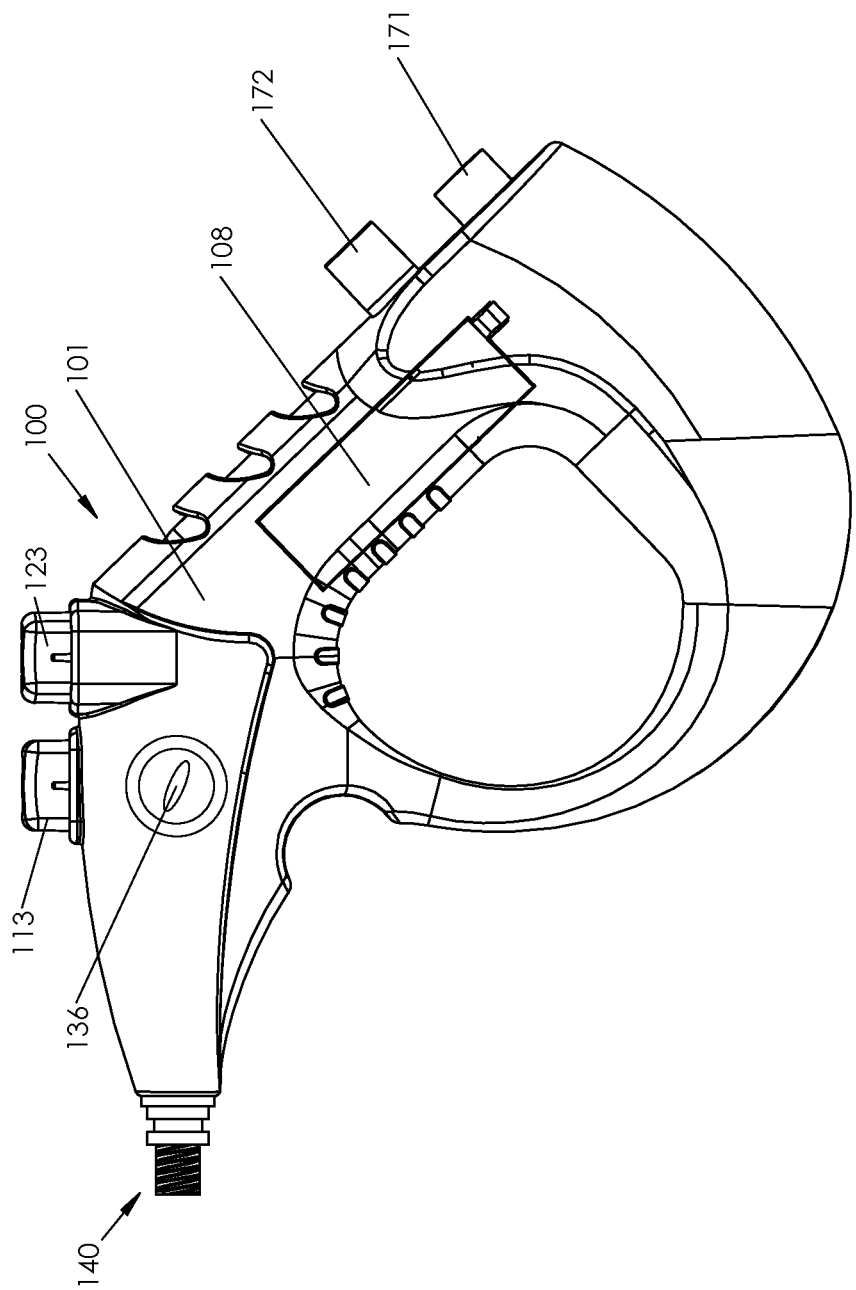
FIG. 6 is a side elevational view illustrating an alternate embodiment of the lavage handle, wherein a rheostat is provided to control a variable intensity of the irrigation-inducing section.
Figure 10:
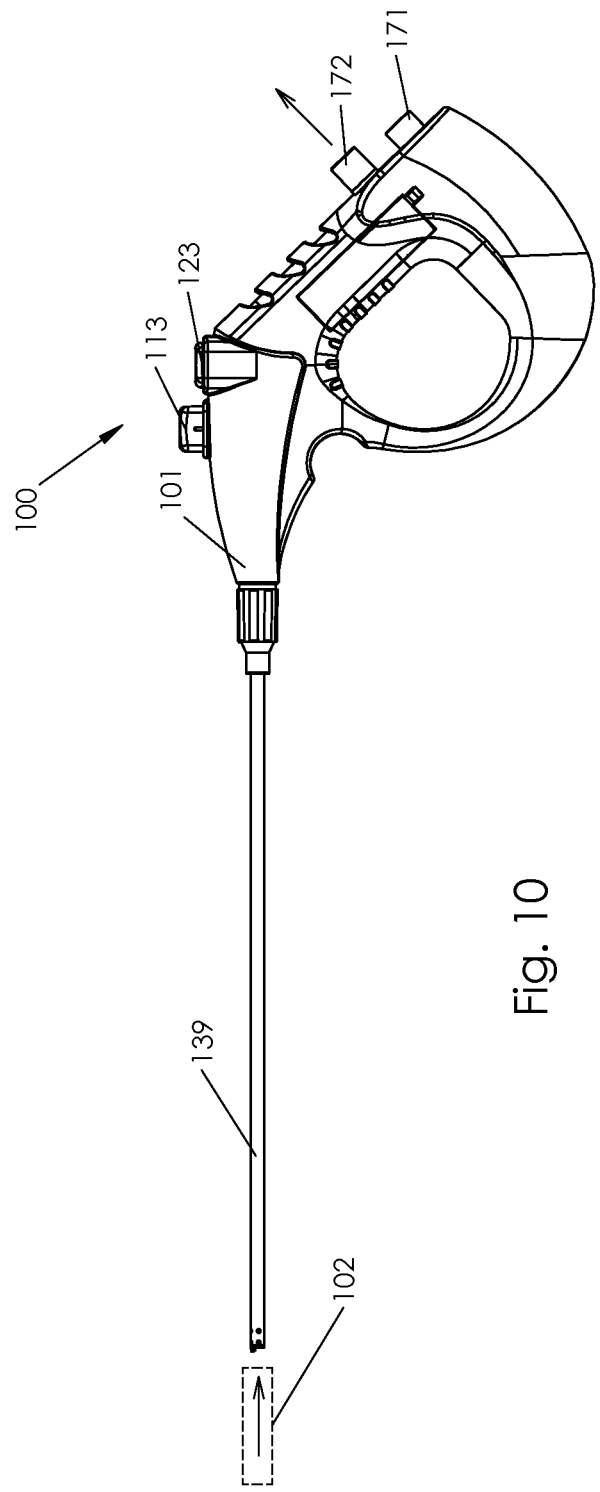
FIG. 10 is a side elevational view of the lavage handle shown in FIG. 1, wherein a directional flow of fluid/debris is shown to ingress a probe removably attached to a probe connector formed at a distal section of the lavage handle.
Figure 11:
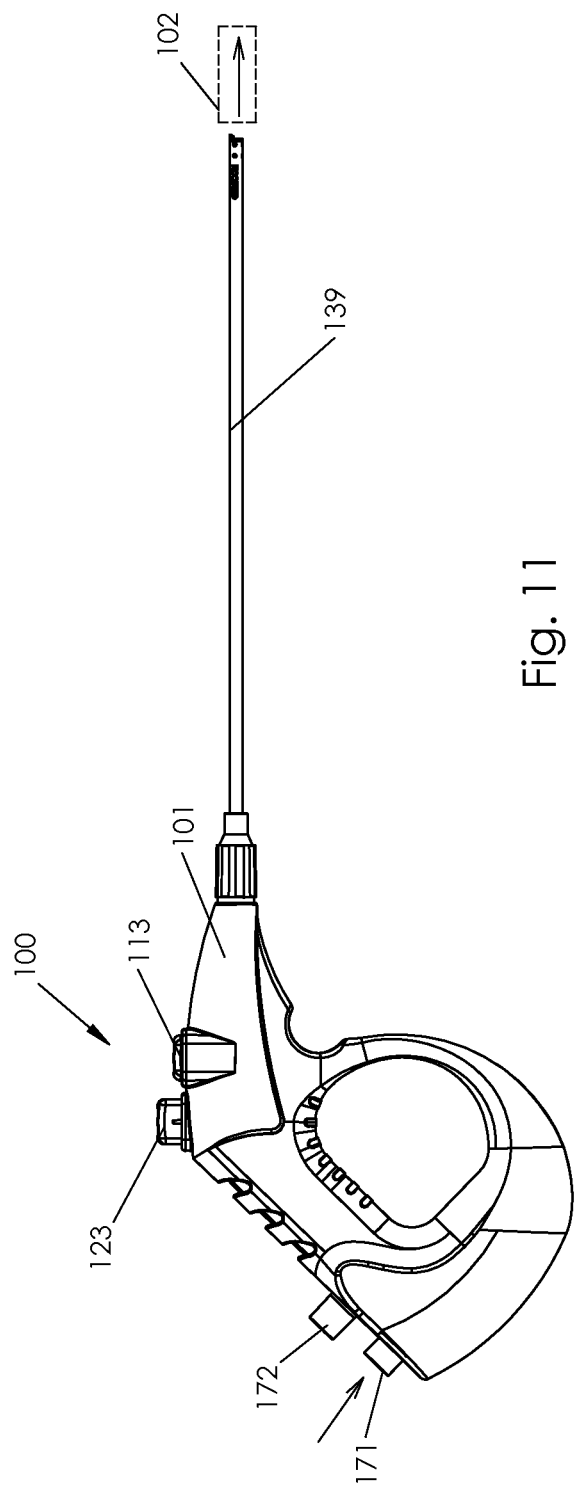
FIG. 11 is a side elevational view of the lavage handle shown in FIG. 1, wherein a directional flow of fluid is shown to egress a suction port formed at a proximal end of the lavage handle.
Figure 12:
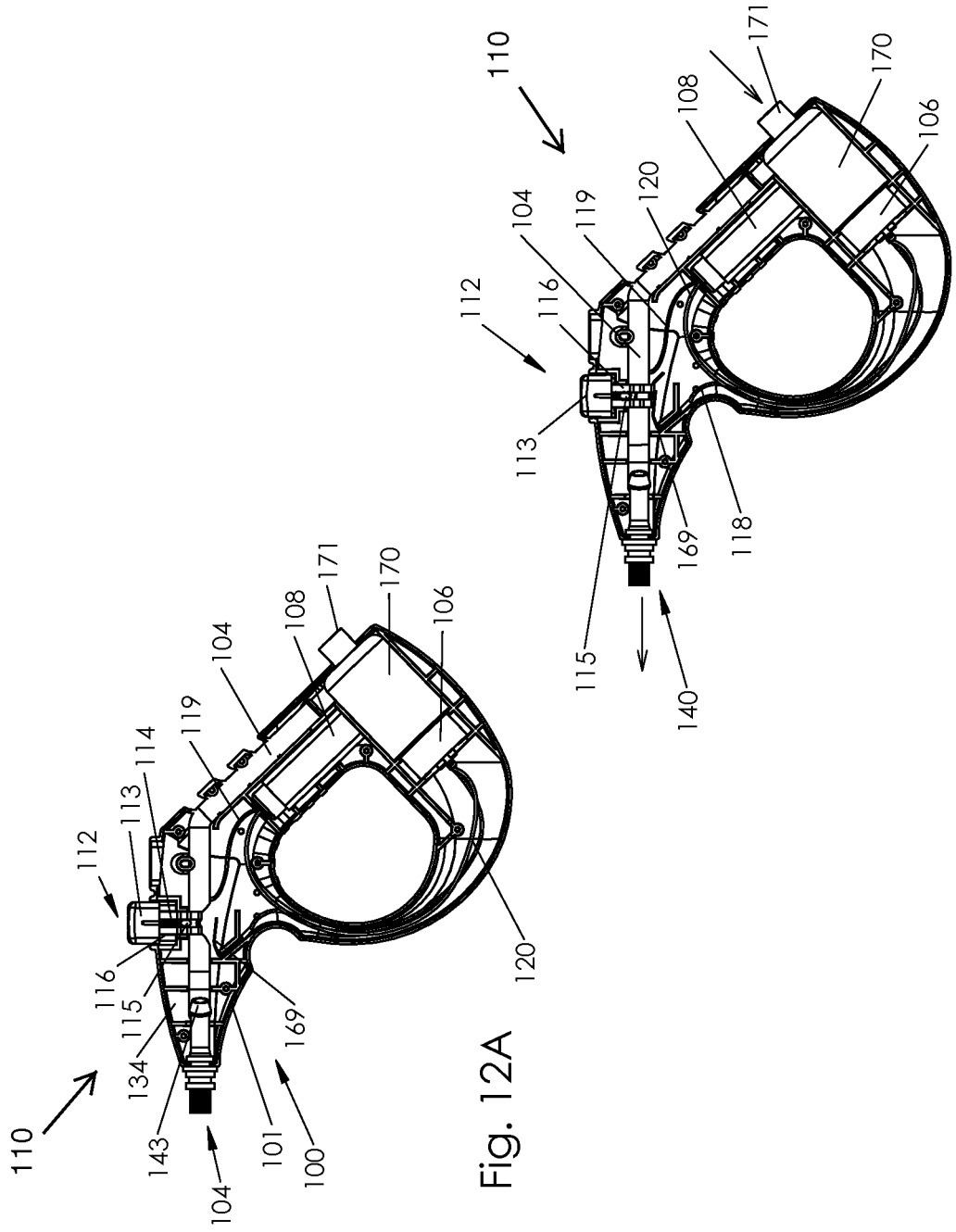
FIG. 12A is a cross-sectional view showing the irrigation side of the lavage handle wherein the irrigation-inducing section is at the raised position thereby causing an open electrical circuit and constriction (e.g., closing) of the irrigation tube.
FIG. 12B is a cross-sectional view showing the irrigation side of the lavage handle wherein the irrigation-inducing section is at the lowered position thereby causing a closed electrical circuit and expansion (e.g., opening) of the irrigation tube.
Figure 13:
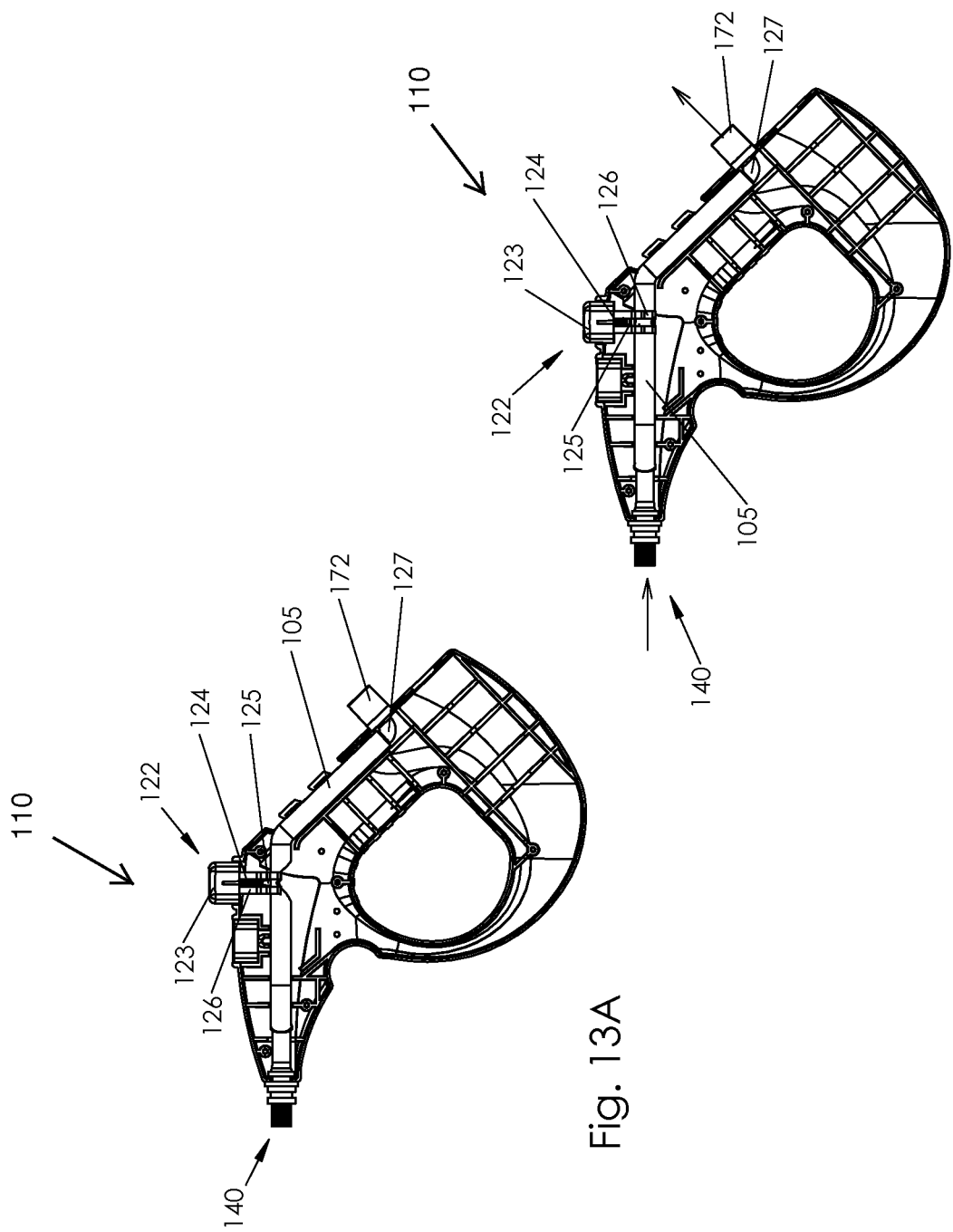
FIG. 13A is a cross-sectional view showing the suction side of the lavage handle wherein the suction-inducing section is at the raised position thereby causing constriction (e.g., closing) of the suction tube.
FIG. 13B is a cross-sectional view showing the irrigation side of the lavage handle wherein the suction-inducing section is at the lowered position thereby causing expansion (e.g., opening) of the suction tube.
Figure 14:
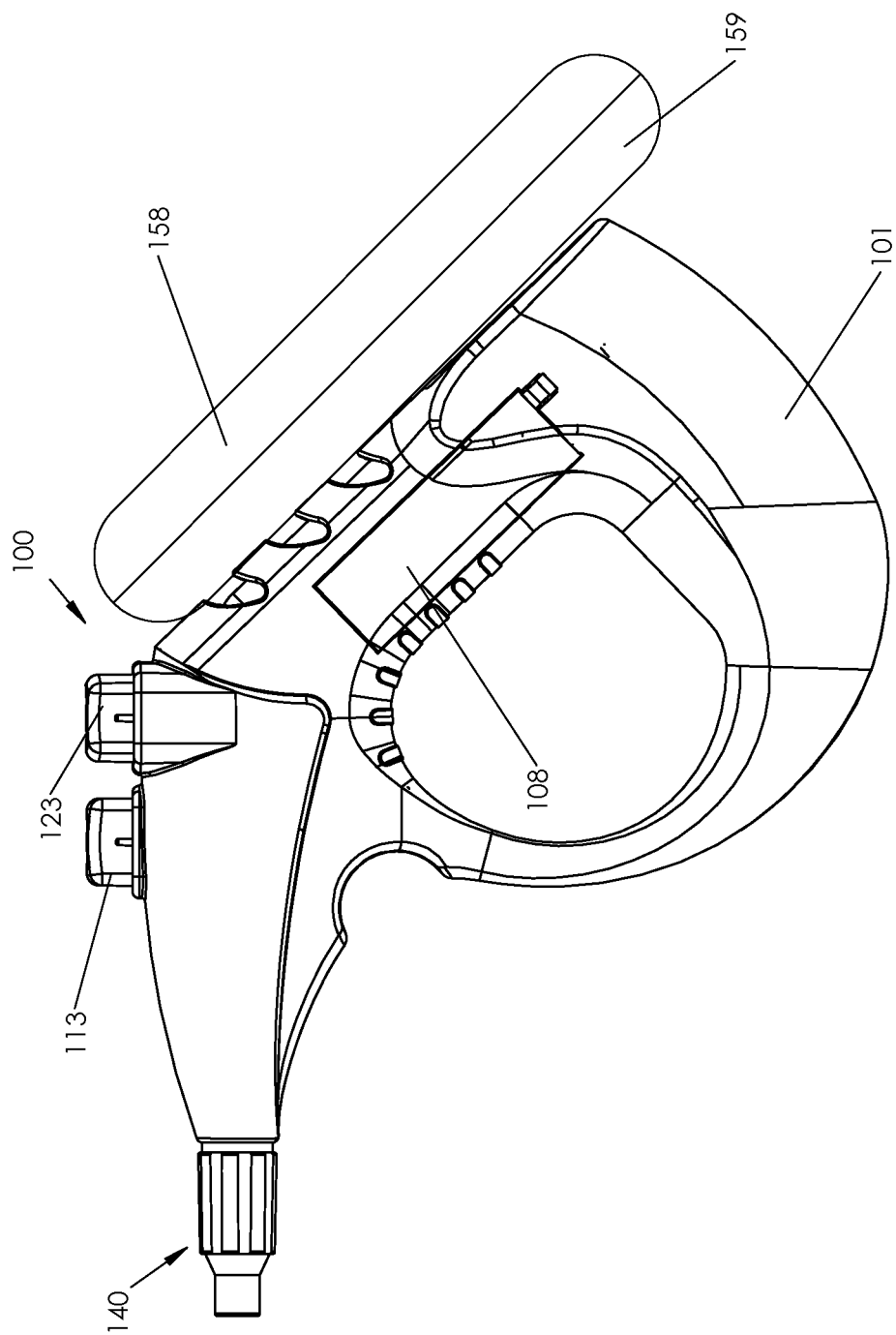
FIG. 14 is a side elevational view showing an irrigation container and a suction container removably coupled to the irrigation connector and suction connector, respectively, of the lavage handle.
Figure 15:
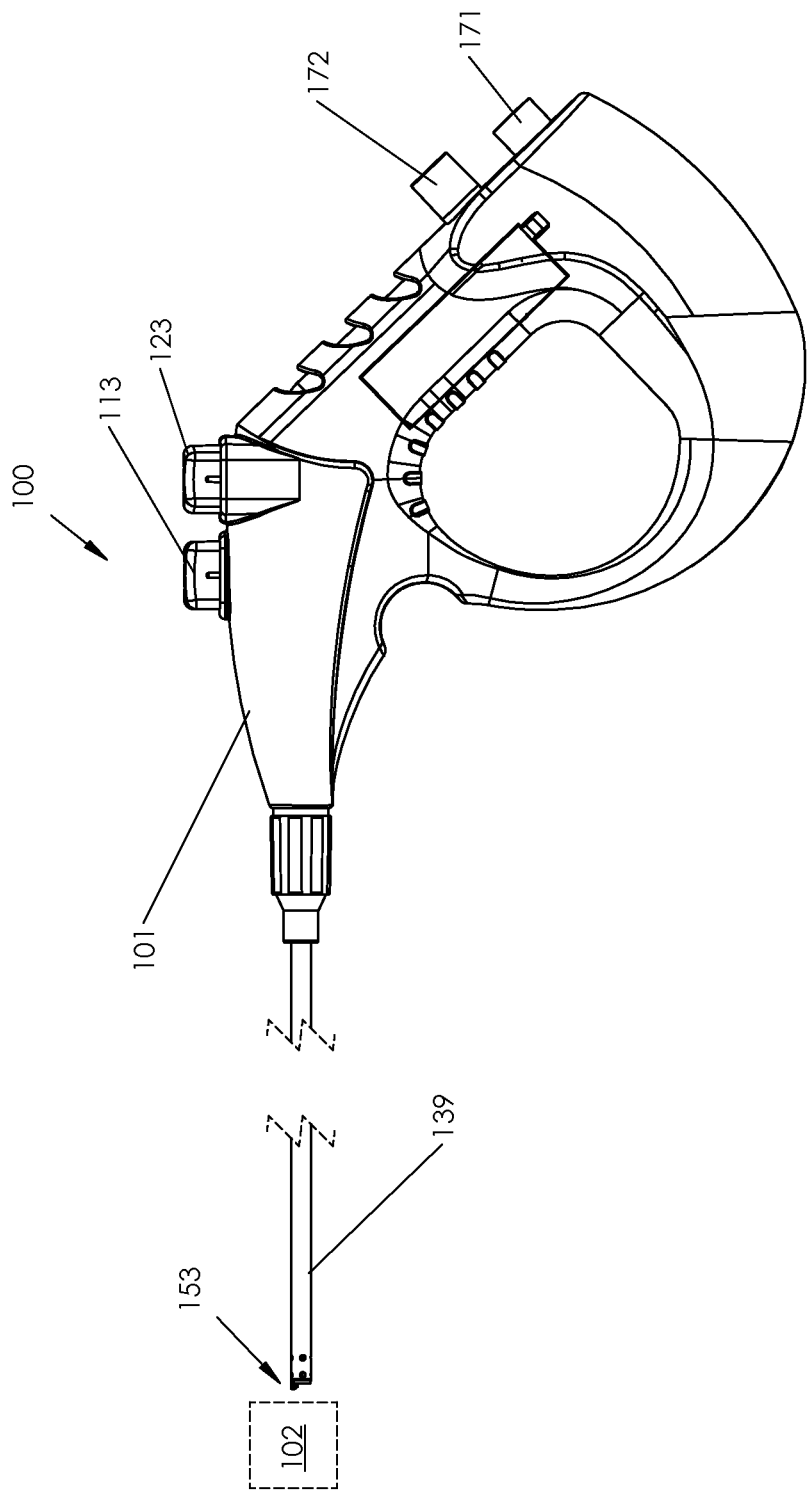
FIG. 15 is a partially broken view of the lavage handle shown in FIG. 14, wherein the optics generating mechanism is positioned proximate to a distal end of a probe employed by the lavage handle.
Figure 16:
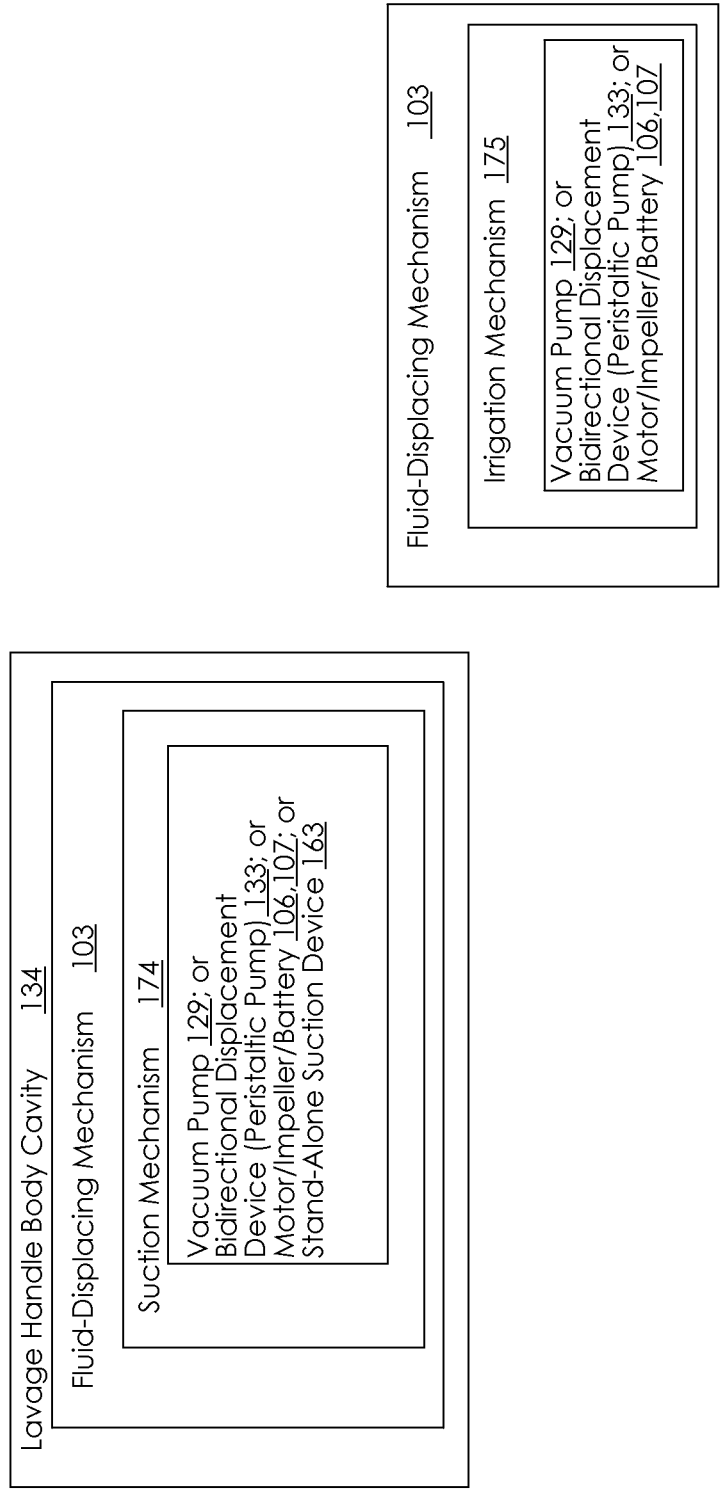
FIG. 16 is a schematic block diagram illustrating a suction function, of the fluid-displacing mechanism, performed by a suction mechanism located interior of the lavage handle, and an irrigation function, of the fluid-displacing mechanism, performed by an irrigation mechanism located exterior the lavage handle, in accordance with non-limiting exemplary embodiments.
Figure 17:
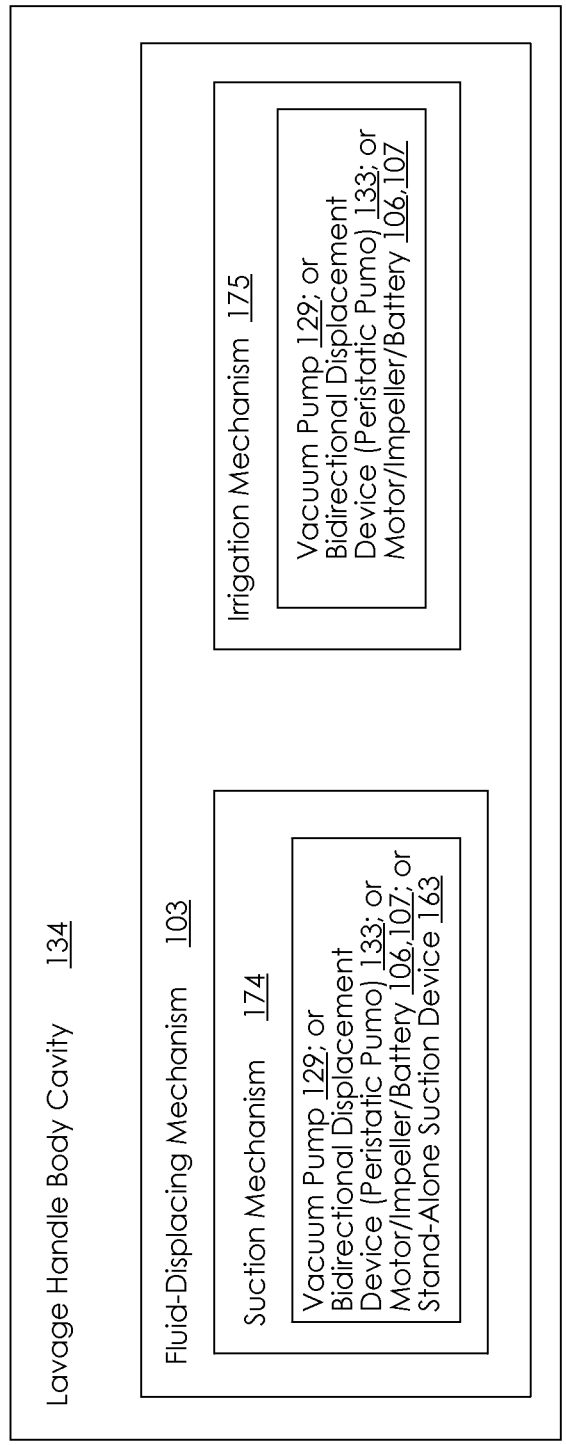
FIG. 17 is a schematic block diagram illustrating an irrigation function and a suction function, of the fluid-displacing mechanism, respectively performed by a suction mechanism located interior of the lavage handle and an irrigation mechanism located exterior the lavage handle, in accordance with non-limiting exemplary embodiments.
Figure 18:
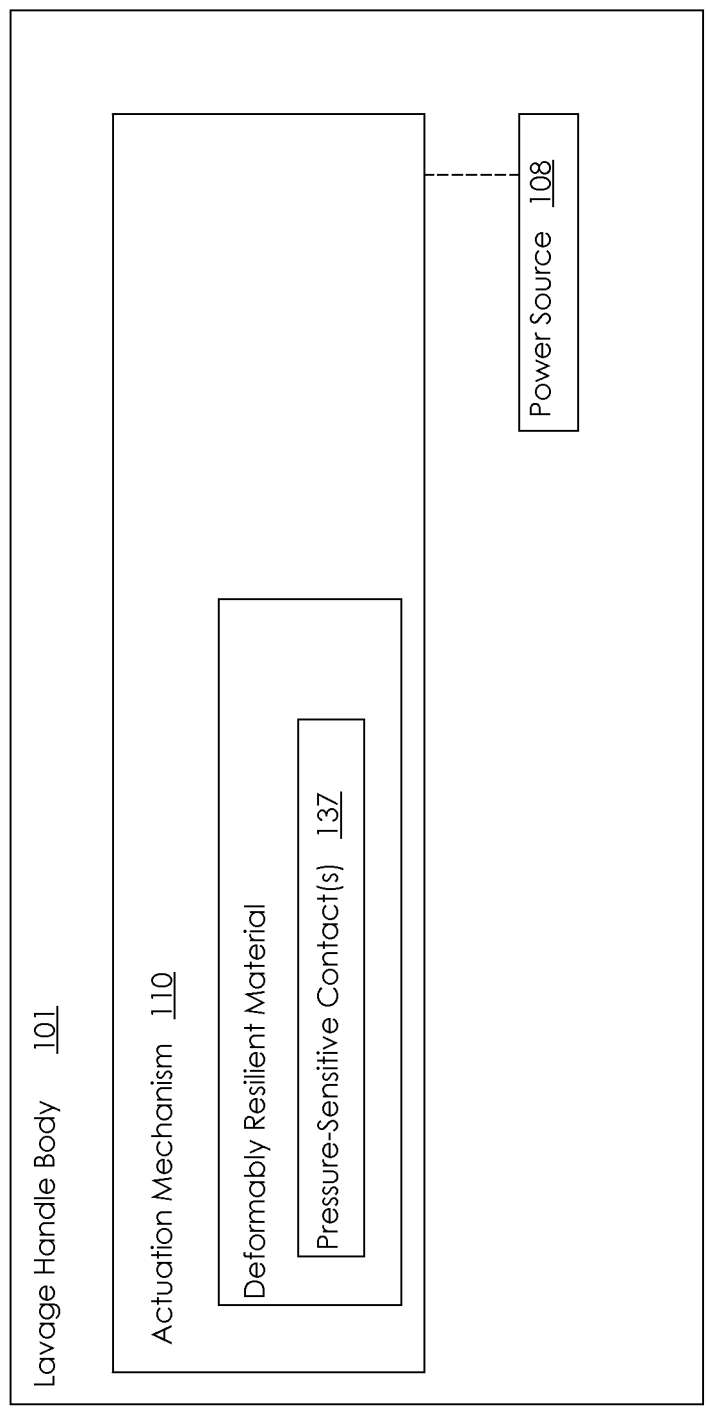
Figure 19:
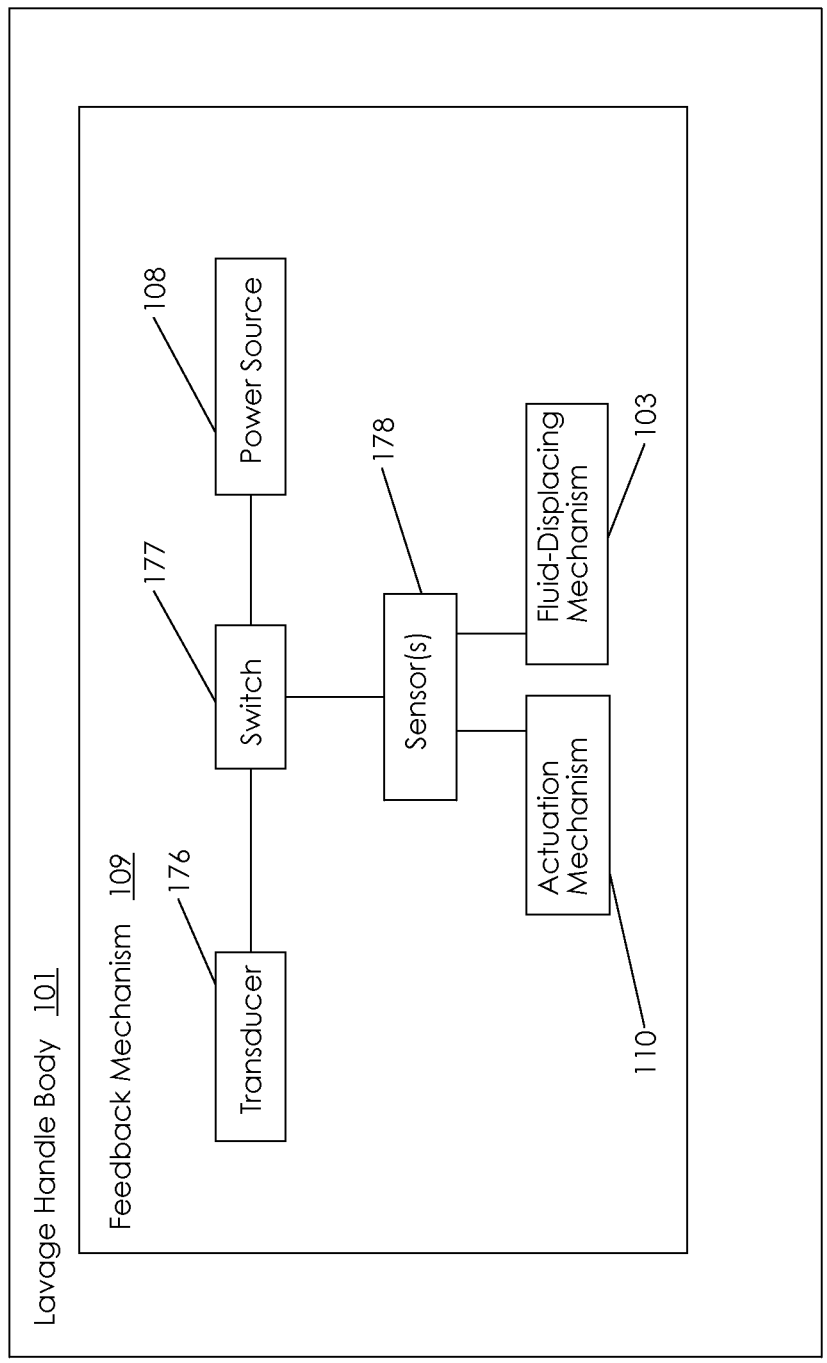
Figure 20A:
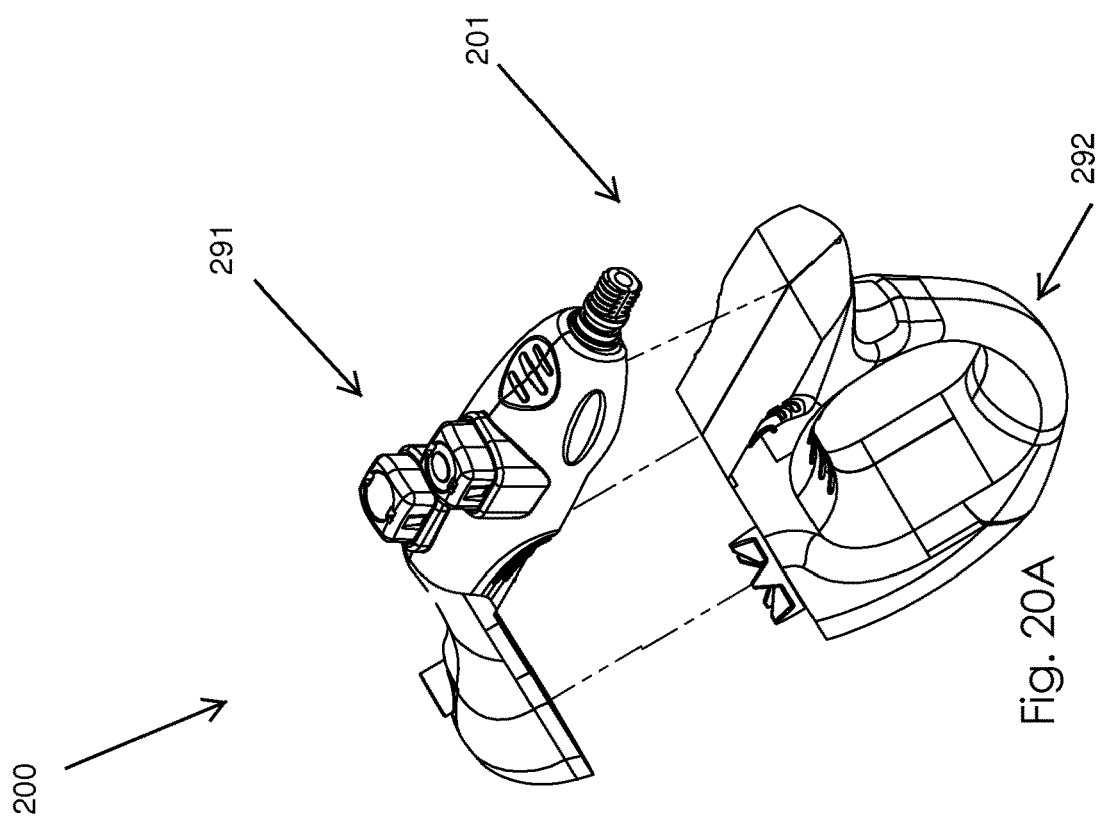
Figure 20:
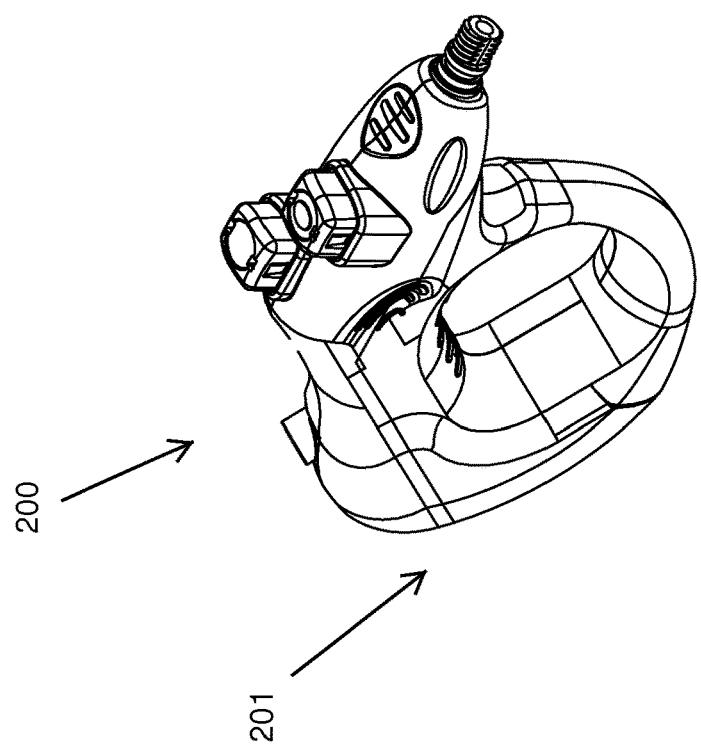
Figure 20B:
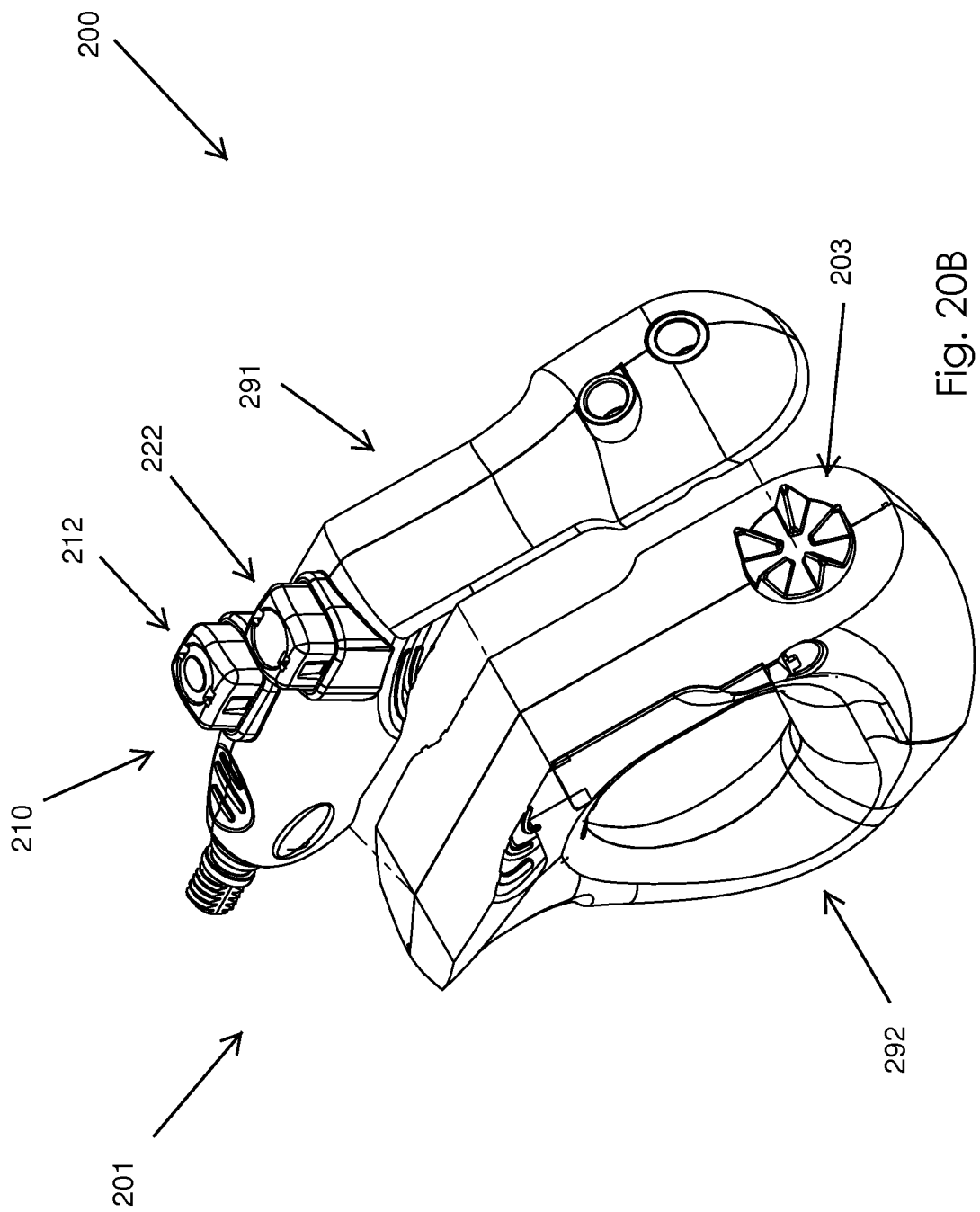

FIG. 18 is a schematic block diagram illustrating an actuation mechanism embodied as deformably resilient material having pressure sensitive contacts located at the lavage handle body, in accordance with a non-limiting exemplary embodiment; and FIG. 19 is a schematic block diagram illustrating the interrelationship between major components of a feedback mechanism located at the lavage handle body, in accordance with a non-limiting exemplary embodiment;

FIG. 20 is a perspective view illustrating a bifurcated lavage handle, in accordance with a non-limiting exemplary embodiment of the present disclosure;

FIG. 20A is a perspective view illustrating a front side of the bifurcated lavage handle shown in FIG. 20, wherein a top portion is separated from a lower portion; and FIG. 20B is a perspective view illustrating a rear side of the bifurcated lavage handle shown in FIG. 20A.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment (s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The terms "suctioning" and "suction" are interchangeably employed throughout this disclosure. The terms "irrigating" and "irrigate" are interchangeably employed throughout this disclosure.

The non-limiting exemplary embodiment(s) is/are referred to generally in FIGS. 1-19 and is/are intended to provide a lavage handle 100 used to discharge fluid (preferably via a propulsion mechanism such as a fluid-displacing mechanism 103) to a target zone 102 and/or retrieve fluid/debris (preferably via a vacuum and/or suction mechanism such as a vacuum pump 129) therefrom, wherein: 1) the fluid-displacing mechanism 103 may include at least one tube 104, 105, a motor 106, an impeller 107, and a power source 108 physically incorporated completely within the lavage handle body 101; 2) the fluid-displacing mechanism 103 can be operated by an actuation mechanism 110 including a resilient spring-actuated irrigation button 113, a switch 177 (e.g., trigger switch, toggle switch, etc.), pressure sensitive contacts 137 (e.g., a squeezable handle body 101 provided with a rheostat 136), which can be located interior/exterior of the lavage handle 100; and 3) a feedback mechanism 109 (e.g., transducer 176, etc.) may be provided to notify the user whether the fluid-displacing mechanism 103 is operating.

Generally speaking, the lavage handle 100 is intended to supply irrigation fluid—from an irrigation fluid supply reservoir 162—into the surgical space (target zone 102) and/or to vacuum fluid/debris from the target zone 102, wherein the fluid-displacing mechanism 103 (e.g., at least one of a motorized impeller 107 and a vacuum pump 129) is physically incorporated within the body 101 of the lavage handle 100. In operation, an actuation mechanism 110 serves as a controller thereby selectively activating/deactivating an operating mode of the fluid-displacing mechanism 103.

In a non-limiting exemplary embodiment, such an irrigation fluid supply reservoir 162 is in fluid communication with the motorized impeller 107 via an external irrigation tube 164 having an irrigation tube connector 160 located at a distal tip thereof. Such a connector 160 is interfaced with the irrigation fluid supply reservoir 162 and affixed at a substantially stable position via use of an irrigation tube fastener 161. As perhaps best shown in FIG. 7B, an external irrigation tube connector 171 as well as an internal irrigation tube connector 121 are both in fluid communication with the motor housing 170, such that fluid/debris are permitted to travel from the fluid supply reservoir 162 downstream through lavage handle body 101 and exit therefrom during irrigation, as needed.

In a non-limiting exemplary embodiment, the fluid-displacing mechanism 103 may also include a stand-alone suctioning device 163 in fluid communication with the body 101 via an external suction tube 165. Such a suctioning device 163 may include a reservoir (e.g., fluid storage container 157) thereat for storing fluid/debris retrieved from target zone 102.

In a non-limiting exemplary embodiment, with reference to, inter alia, FIGS. 8A-8D, the actuation mechanism 110 may include an irrigation-inducing section 112 that includes an irrigation button 113, a resilient irrigation spring 114 having a top end engaged with the irrigation button 113, a stationary irrigation pin 115 engaged with a bottom end of the resilient irrigation spring 114, and an irrigation tube clamp 116 receiving the stationary irrigation pin 115 and resilient irrigation spring 114. The stationary irrigation pin 115 is anchored to an internal surface of the body 101 of the lavage handle 100. The irrigation button 113 is attached to the irrigation tube clamp 116 such that the resilient irrigation spring 114 and stationary irrigation pin 115 are intercalated therebetween. When no external force is acting on the irrigation button 113, the resilient irrigation spring 114 is released to a less tensioned position thereby urging the irrigation tube clamp 116 upwards towards the stationary irrigation pin 115. Thus, the irrigation tube 104 is pinched and is not permitted to channel fluid therethrough. In particular, the irrigation tube 104 is pinched between the stationary irrigation pin 115 and a bottom surface of the irrigation tube clamp 116. Conversely, when irrigation button 113 is compressed, the resilient irrigation spring 114 is compressed to a more tensioned position and the irrigation tube clamp 116 is lowered relative to the stationary irrigation pin 115. Such movement causes the irrigation tube 104 to decompress (e.g., open) and allows water to flow outwardly via a probe 139 attached to the distal end 146 of the lavage handle 100. Notably, the stationary irrigation pin 115 remains statically disposed at a fixed position while the irrigation button 113 and irrigation tube clamp 116 synchronously move up and down—upon compression and expansion of the resilient irrigation spring 114—relative to the stationary irrigation pin 115 and irrigation tube 104. In this manner, the irrigation button 113 and irrigation tube clamp 116 reciprocate along a linear path (e.g., suction button path 166) at least substantially orthogonal to a plane defined parallel along the stationary irrigation pin 115.

In a non-limiting exemplary embodiment, with further reference to FIGS. 7A-7B and 12A-12B, the irrigation-inducing section 112 may include an electrically-conductive arm 117 that protrudes outwardly from the irrigation tube clamp 116. Such an arm 117 serves as a circuit contact and may be registered orthogonal to the stationary irrigation pin 115 thereby lying along a plane 168 subjacent thereto. The arm 117 comes into communication with electrical leads 118 (e.g., battery wire 119, motor wire 120) respectively connected to the battery 108 and motor 106 of the fluid-displacing mechanism 103. In particular, when the irrigation button 113 is compressed, the arm 117 engages a connector spring 169 (e.g., conductive contact, terminal, etc.) supported at the interior of the lavage handle 100 thereby closing an electrical circuit between the battery wire 119 and motor wire 120, which are in electrical communication with the battery 108 and motor 106 of the fluid-displacing mechanism 103. Activation of the motor drives the impeller 107, which causes fluid to flow outwardly through the irrigation tube 104 and egresses probe 139 until the electrical circuit is opened and the irrigation tube 104 is pinched—by releasing the irrigation button 113. In particular, when the irrigation button 113 is released, the arm 117 is disconnected from the connector spring 169 and the irrigation tube clamp 116 restrains (e.g., pinches) the internal irrigation tube 104 against the stationary irrigation pin 115 thereby preventing further irrigation discharge. Use of a seal ring 156 ensures fluid/debris does not pass beyond the impeller 107 and escape the motor housing 170.

In a non-limiting exemplary embodiment, as perhaps best shown in FIGS. 9A-9D, the actuation mechanism 110 further includes a suction-inducing section 122 that operates in a similar manner as the irrigation-inducing section 112. Such a suction-inducing section 122 opens/closes the internal suction tube 105, which is in communication with the fluid-displacing mechanism 103. For example, the suction-inducing section 122 includes a suction button 123, a resilient suction spring 124, a stationary suction pin 125 and a suction tube clamp 126 operationally interconnected in a substantially similar manner as described hereinabove for the irrigation-inducing section 112. It is noted that the suction function 174 (e.g., FIGS. 13A, 13B) may be driven by motor 106, impeller 107 and battery 108, in which case an electrically conductive arm 117 similar to arm 117 would be added to the suction button 123. However, if the suction function 174 (e.g., FIGS. 13A, 13B) is effectuated by a separate stand-alone suctioning device 163, power may be independently supplied thereto by an external power source. In such an embodiment, an electrically conductive arm 117 would not be employed.

In this manner, in a non-limiting exemplary embodiment, the suction function 174 (e.g., FIGS. 13A, 13B) of the fluid-displacing mechanism 103 may be effectuated by a vacuum pump (e.g., stand-alone suctioning device 163) located exterior of the lavage handle 100. Such a vacuum pump 129 may be powered by an external power source and independently operated from the irrigation function 175 (e.g., FIGS. 12A, 12B) of fluid-displacing mechanism 103. In a non-limiting exemplary embodiment, the vacuum pump may be comprised of the motor 106 and impeller 107 or another suitable device such.

In a non-limiting exemplary embodiment, the irrigation function 175 (e.g., FIGS. 12A, 12B) of the fluid-displacing mechanism 103 may be effectuated by a mechanism located exterior of the lavage handle 100 while the suction function 174 (e.g., FIGS. 13A, 13B) of the fluid-displacing mechanism 103 may be effectuated by a mechanism located entirely within the lavage handle 100.

In a non-limiting exemplary embodiment, both the irrigation function 175 (e.g., FIGS. 12A, 12B) and suction function 174 (e.g., FIGS. 13A, 13B) may be effectuated by one or more mechanisms located entirely interior the lavage handle 100, such as a peristaltic pump 138 arrangement where irrigation is achieved by a clockwise rotation of the impeller 107 and suction is achieved by an opposite counter clockwise rotation of the impeller 107.

The fluid-displacing mechanism 103 can serve one or more functions—irrigation function 175 (e.g., FIGS. 12A, 12B) and suction function 174 (e.g., FIGS. 13A, 13B)—and may be effectuated by one or more sections of the actuation mechanism 110 (e.g., irrigation-inducing section 112, suction-inducing section 122), which can be located interior and/or exterior of the lavage handle 100, respectively.

In a non-limiting exemplary embodiment, with reference to FIGS. 1-19, the fluid-displacing mechanism 103 includes an internal irrigation tube 104, a motor 106, an impeller 107 and a power source 108 housed within the lavage handle 100. The actuation mechanism 110 includes an irrigation-inducing section 112 preferably including an irrigation button 113 having an electro-conductive irrigation tube clamp 116 that serves at least two functions. First, the irrigation tube clamp 116 pinches/releases the internal irrigation tube 104 for restraining/freeing fluid flow. Second, the irrigation tube clamp 116 engages/disengages an electrical contact (e.g., connector spring 169) for closing/opening a circuit thereby powering the motor 106 and impeller 107. Cooperation of such components enables selective operation of irrigation function 175 (e.g., FIGS. 12A, 12B) of the fluid-displacing mechanism 103. Thus, such an embodiment can open/close the battery 108 circuit without employing the electro-conductive arm 117 because the irrigation tube clamp 116 is electro-conductive.

In a non-limiting exemplary embodiment, the suction function 174 (e.g., FIGS. 13A, 13B) of the fluid-displacing mechanism 103 may include a vacuum pump 129 (e.g., stand-alone suctioning device 163) located external to the lavage handle 100. Such a vacuum pump 129 may be powered via an external power source and interfaced with an internal suction tube 105, (via elbow coupling 127, external suction tube connector 172 and external suction tube 165), traveling through the lavage handle 100. Notably, the internal suction tube 105 is isolated from the internal irrigation tube 104 and travels along a mutually exclusive and non-overlapping path 131 relative to path 130 of the internal irrigation tube 104. The suction function 174 (e.g., FIGS. 13A, 13B) is effectuated by a suction-inducing section 122 of the actuation mechanism 110. Such a suction-inducing section 122 opens/closes the internal suction tube 105 in a substantially similar manner as the irrigation-inducing mechanism 112 opens/closes the internal irrigation tube 104, explained hereinabove.

In a non-limiting exemplary embodiment, the fluid-displacing mechanism 103 may employ a bidirectional displacement device 133 (e.g., peristaltic pump 138) located interior of the lavage handle 100.

In a non-limiting exemplary embodiment, the fluid-displacing mechanism 103 may employ a bidirectional displacement device 133 (e.g., peristaltic pump 138) located exterior of the handle.

In a non-limiting exemplary embodiment, the lavage handle 100 may include a portable body 101 having a cavity 134 formed therein, the fluid-displacing mechanism 103 can be located within the cavity 134 wherein the fluid-displacing mechanism 103 has one of a first operating mode for discharging (e.g., irrigating) fluid towards the target zone 102 and a second operating mode for retrieving (e.g., suctioning) fluid/debris from the target zone 102. The actuation mechanism 110 is attached to the body 101 and communicatively coupled to the fluid-displacing mechanism 103. In this manner, the actuation mechanism 110 selectively changes the fluid-displacing mechanism 103 between at least one of the first operating mode (irrigation) and the second operating mode (suction) upon receiving a corresponding user input. Of course, the actuation mechanism 110 may be operated in variable speed (e.g., via rheostat 136) as desired.

In a non-limiting exemplary embodiment, the actuation mechanism 110 is disposed at least partially exterior of the body 101. For example, the actuation mechanism 110 may include a suction-inducing section 122 having a suction button 123 and an irrigation-inducing section 112 having an irrigation button 113. It is noted that use of the term "button" is done merely for simplicity. One skilled in the art understands such "buttons" may include a variety of suitable implements that can be readily identified and depressed by the user. For example, in a non-limiting exemplary embodiment, the actuation mechanism 110 includes a multi-pole toggle switch 177. In another non-limiting exemplary embodiment, the actuation mechanism 110 includes at least one rheostat 136. In yet another non-limiting exemplary embodiment, the actuation mechanism 110 includes a spring resistive trigger.

In yet another non-limiting exemplary embodiment, the actuation mechanism 110 is disposed entirely interior of the body 101 wherein the body 101 is formed from deformably resilient (e.g., squeezable) material. In a non-limiting exemplary embodiment, the actuation mechanism 110 includes a pressure-sensitive contact 137 in communication with the deformably resilient material such that the actuation mechanism 110 is displaced to electrically engage the power source 108 when the body 101 is biased to a tensioned state. For example, by squeezing a first predefined region of the body 101, the electrical pressure-sensitive contact 137 engages the power source 108 and closes an electrical circuit thereby powering the fluid-displacing mechanism 103. When a second predefined region of the body 101 is squeezed, the fluid-displacing mechanism 103 is deactivated by separating the contact from the power source 108. Such a function may be similar to a toggle switch. Alternately, a single region of the lavage handle 100 may be squeezed a first time to activate the fluid-displacing mechanism 103, and thereafter squeezed a second time to deactivate the fluid-displacing mechanism 103. Furthermore, a sliding trigger (e.g., rheostat 136) may be employed wherein displacement of the trigger, along a predefined path, causes variable intensity of the fluid-displacing mechanism 103.

In a non-limiting exemplary embodiment, the lavage handle 100 further includes a feedback mechanism 109 in communication with the fluid-displacing mechanism 103, for notifying the user whether at least one of the first and second operating modes (e.g., suction function 174, irrigation function 175) is active. Such a feedback mechanism 109 may include sensors 178 in communication with the fluid-displacing mechanism 103 wherein, upon detecting operation of the fluid-displacing mechanism 103, such sensors 178 emit signals to close a circuit between the feedback mechanism 109 and a power source 108. In this manner, the feedback mechanism 109 is automatically switched between on and off modes when the fluid-displacing mechanism 103 is operating and not-operating, respectively, thereby providing automatic and real-time detection.

In a non-limiting exemplary embodiment, the feedback mechanism 109 includes at least one transducer 176 for generating and emitting at least one alert signal when the fluid-displacing mechanism 103 is active at one of the first (e.g., irrigation) and second (e.g., suction) operating modes.

In a non-limiting exemplary embodiment, the at least one alert signal is selected from the group including an audio signal, a visual signal, a mechanical signal, a sensory signal and a combination thereof.

In a non-limiting exemplary embodiment, the feedback mechanism 109 is located interior of the body 101. For example, a haptic feedback mechanism 109 may be employed wherein mechanical signals cause the handle body 101 to vibrate or otherwise oscillate during use.

In a non-limiting exemplary embodiment, the feedback mechanism 109 is located at least partially exterior of the body 101. For example, a visual feedback mechanism 109 may be employed wherein optical signals (e.g., diodes) cause the handle body 101 to illuminate or otherwise change color during use.

In a non-limiting exemplary embodiment, the fluid-displacing mechanism 103 includes a pump having a motor 106 and an impeller 107 communicatively coupled thereto. Suitable drive mechanisms for the pump may include an electromechanical actuator (e.g., servomotor 106) having a control member that is designed to generate fluid flow in the suction direction and/or irrigation direction. A change in the position of the control member produces a change in the flow of energy to the lavage handle 100 and thereby affects the suction 174 and/or irrigation 175 functions. The fluid-displacing mechanism 103 may be fueled by an internal power source 108 (e.g., DC battery 108) located within the body 101 of the handle.

Of course, the power source 108 may include one or more rechargeable or non-rechargeable disposable batteries, photovoltaic cells, and/or an AC adapter or other power supply means. As noted above, a rheostat 136 may be employed to variably adjust the energy flow thereby increasing and/or decreasing the intensity of suction 174 and/or irrigation 175 functions (e.g., FIGS. 12A, 12B).

In a non-limiting exemplary embodiment, the internal suction tube 105 and the internal irrigation tube 104 separately direct fluid and/or debris along mutually exclusive paths 130, 131 relative to a probe connector 140 (e.g., adaptor). Such a probe connector 140 is attached to a port that is located at a distal end 146 of the lavage handle 100. The probe connector port 141 serves both as an inlet and an outlet for the fluid-displacing mechanism 103. The mutually exclusive paths 130, 131 each travel away from the probe connector port 141, and towards an external suction tube connector 172 and an external irrigation tube connector 171 both located at a proximal end 147 of the lavage handle 100, respectively.

In a non-limiting exemplary embodiment, the probe connector port 141 defines a single distal opening that diverges proximally away therefrom. In this manner, the probe connector port 141 proximally bifurcates into suction connector port 142 attached to proximal suction opening 144 and, irrigation connector port 143 attached to proximal irrigation opening 145, which respectively connect to the internal suction tube 105 and internal irrigation tube 104. In this manner, fluid and/or debris is vacuumed away from the target zone 102 via the internal suction tube 105 towards a proximal end 147 of the handle. Conversely, fluid is discharged toward the target zone 102 via the internal irrigation tube 104, away from the proximal end 147 of the handle. Advantageously, vacuumed fluid/debris is collected in a first reservoir 148 (e.g., fluid-storage container 157), while irrigated fluid is supplied from a second reservoir 149 (e.g., supply reservoir 162).

Although the preferred embodiment of the fluid-displacing mechanism 103 includes a motor 106 and impeller 107, other suitable fluid-displacing mechanism(s) 103 may be employed without departing from the true spirit and scope of the present disclosure. For example, suitable fluid-displacing mechanism(s) 103 may include hydraulic, pneumatic, or electrical drives. Diaphragm and piston drives may also be employed. Other suitable configurations may include an induction motor 106, an electromagnet (e.g., solenoid) motor 106. Yet further, the fluid-displacing mechanism 103 may be powered by piezoelectric energy; conversion of potential (e.g., stored) energy to kinetic (e.g., hydrodynamic) energy; pneumatic energy; and/or gas (e.g., CO2) canisters, etc.

In a non-limiting exemplary embodiment, the lavage handle 100 may further include a user interface 150, and a voice-activated mechanism 151 operatively coupled to the actuation mechanism 110. In this manner, upon receiving a user input signal, the user interface 150 generates and transmits a corresponding control signal to the voice-activated mechanism 151 for operating the actuation mechanism 110.

In a non-limiting exemplary embodiment, the lavage handle 100 may further include a flow-monitoring mechanism 152 in communication with the power-operated fluid-displacing mechanism 103. Such a flow-monitoring mechanism 152 monitors at least one of a flow pressure, flow rate, and a volume of the fluid passing through the body 101.

In a non-limiting exemplary embodiment, the lavage handle 100 may further include an optics-generating mechanism 153 in communication with the body 101. Such an optics-generating mechanism 153 includes at least one of a light source for illuminating the target zone 102 and a camera for capturing a visual image of the target zone 102.

In a non-limiting exemplary embodiment, the optics-generating mechanism 153 may include one or more LEDs located at the probe 139 and operably coupled to the present disclosure's processing and signal generation components and can be configured to controllably flash, if desired. The disclosure is not limited to any restricted number or arrangement of LEDs. Any number and arrangement of LEDs could be provided, within the limits of the present disclosure's structure and components. The LEDs may flash if a triggering event is detected, for example. Additionally, any flashing patterns could be used. The LEDs could flash in harmony, randomly or sequentially, or groups (e.g., rows) could flash sequentially, randomly or alternately, or in any other manner likely to attract attention. One or more processing devices and one or more LED drivers manages flashing of the LEDs according to predetermined or user-specified data and instructions. One skilled in the art understands any number of suitable light sources may be employed, without departing from the true scope and spirit of the present disclosure.

In a non-limiting exemplary embodiment, one or more of the voice-activated mechanism(s) 151, fluid-monitoring mechanism 152 and optics-generating mechanism 153 may be wirelessly operated, and include user interface 150, a communication device 154 and display screen 155, for example. All or some of these components may be stand-alone components or at least partially incorporated into the body 101 of the lavage handle 100.

In a non-limiting exemplary embodiment, the user interface 150 may include a variety of stand-alone or shared devices that are capable of generating and transmitting a control signal upon receiving a user input. For example, exemplary user interface 150 devices may include a remote controller employing RF, infra-red, acoustic or cellular technology, as well known in the industry. In alternate embodiments, the user interface 150 may include a handheld computer, a PDA, a cell phone, a keyboard, a mouse, etc. that may be comprised of commercially available hardware and software operating systems, for example. The aforementioned user interfaces are intended to represent a broad category of exemplary user interfaces capable of functioning in accordance with the present disclosure. Of course, the user interfaces may include other components, peripherals and software applications provided they are compatible and capable of cooperating with remaining devices of the present disclosure. In addition, the user interfaces may include information, documents, data and files needed to provide functionality and enable performance of methodologies in accordance with exemplary embodiment(s) of the disclosure.

In a non-limiting exemplary embodiment, the display screen 155 is configured for displaying various amounts of textual and/or graphical information. The display screen 155 may be monochrome or color, of various physical dimensions, of various types. In one embodiment, the display may be suitable for displaying full motion video in color. By way of example and not limitation, the display may be comprised of a liquid crystal display (LCD); a field emission display FED; so called "E-ink" technologies, which employ microspheres having at least two reflectance states; a cathode-ray tube (CRT) display; a gas plasma display; an LED readout configured to display alpha-numeric and graphical information; or any other compatible visual display device. In a preferred implementation, the display screen 155 is large enough to display, with clarity, one or more lines of information. Optionally, the display screen 155 may be configured with a touch-screen interface, to present a user with a graphical user interface 150.

In a non-limiting exemplary embodiment, the communication device 154 may communicate with the user interface 150 using one or more wirelessly LAN (WLAN) protocols, using low power, ultra-wide band (UWB) communication signals or some other type of wireless signals for RF or optical (e.g., infrared) communication of information to the flow-monitoring mechanism 152 and voice-activated mechanism 151. A real-time WLAN protocol or a standard wireless LAN protocol such as that of IEEE 802.11, BLUETOOTH® or IRDA may be used without departing from the scope of the present disclosure. A local network that connects the communications device to a respective local computer system may, for example, include a single, unified full duplex LAN, such as a 100 BaseT Ethernet LAN. Alternatively, the local network may include two or more interconnected LANs or other network communications means. Any of a variety of other types of computer systems and associated applications may be provided on the network employed by the present disclosure.

Optionally, various ports and interfaces may be provided to communicate with peripherals, subsystems and systems. Such devices may include serial ports for bi-directional communications, and/or an optical communications (e.g., infrared) port for wireless line of sight communications. Other ports may include parallel and USB ports.

In addition to having a communications module, which may employ RS232, RS422, Ethernet, 802.11, IRDA, or any other protocol used to exchange data between the user interface 150, flow-monitoring mechanism 152 and voice-activated mechanism 151, the communications device may have a microcontroller, which acts as a protocol converter for conversion between a protocol used to communicate with the user interface 150, and a protocol used to communicate with the flow-monitoring mechanism 152 and voice-activated mechanism 151. In other embodiments, the microcontroller could be another PC, or even a separate process, such as a process that communicates through a PCI interface board. The microcontroller may have an internal clock oscillator that provides a time base for all serial communication operations. Alternatively, a crystal and associated circuitry may be utilized for a timing base. Those skilled in the art will appreciate that any device capable of timing and controllably directing data from stored memory to output ports for communication in a compatible format to the flow-monitoring mechanism 152 and voice-activated mechanism 151 could be used and is intended to come within the scope of the disclosure.

In a non-limiting exemplary embodiment, the communication device 154 can wirelessly communicate over a cellular network capable of sending out control and response signals. Further, the communication device 154 can use any communication network that allows the care provider to learn the threat level of the triggering event via a detection signal. For example, very low frequency signals or radio signals could be used to communicate between the patient and care provider.

In a non-limiting exemplary embodiment, the present disclosure may employ the cellular communication network, such as the AMPS (Advanced Mobile Phone System) cellular system, which is the analog cellular system used in the United States. In another embodiment, the present disclosure may be coupled via network connectivity among the various wireless communication components.

The present disclosure (system, process, or any part(s) thereof) may be implemented using hardware, software or a combination thereof and may be implemented in one or more communication systems or other processing systems. In fact, in one embodiment, the disclosure is directed toward one or more communication devices capable of carrying out the functionality described herein. The communication device(s) include one or more processors.

In a non-limiting exemplary embodiment, the processor may be connected to a communication infrastructure, such as transceivers (e.g., components of the user interface 150, flow-monitoring mechanism 152, and voice-activated mechanism 151). After reading this description, it will become apparent to a person skilled in the relevant art(s) how to implement the disclosure using other communication systems and/or network architectures.

In a non-limiting exemplary embodiment, a main memory is provided that includes, for example, a removable memory chip (such as an EPROM, or PROM) and associated socket, and other removable storage units and interfaces which allow software and data to be transferred from the removable storage unit to the communication device 154 and/or user interface 150.

In this document, the terms "programmable software instructions" and "control logic algorithm" are used to generally refer to chronological operating steps that are stored memory and signals, for example. These programmable software instructions are means for providing instructions to the system of the present disclosure. The disclosure is directed to such programmable software instructions.

The programmable software instructions (control logic algorithms) are stored in a main memory. The programmable software instructions may also be received via a suitable communications interface. Such programmable software instructions, when executed, enable the user interface 150, flow monitoring device 152 and voice-activated device 151 to perform the features of the present disclosure as discussed herein. In particular, the programmable software instructions, when executed, enable the processor to perform the features of the present disclosure. Accordingly, such programmable software instructions represent controllers of the present system.

In a non-limiting exemplary embodiment, where the disclosure is implemented using software, the software may be stored in a memory and loaded into the user interface 150 using a conventional communications interface. The control logic algorithm (software), when executed by the processor, causes the processor to perform the functions of the disclosure as described herein.

In a non-limiting exemplary embodiment, the disclosure is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the disclosure is implemented using a combination of both hardware and software.

In a non-limiting exemplary embodiment, the voice-activated mechanism 151 may be connected through an interface to an input port of a processor (e.g., at the user interface 150 and/or lavage handle 100). The voice-activated mechanism 151 is constructed to receive sounds and through a microphone or equivalent acoustic transducer and compare the acoustic information received with information stored in permanent memory in the voice recognition device or the processor representative of the sounds corresponding to a vocabulary of key words necessary for voice operation of the suction function 174 and/or irrigation function 175. Upon recognizing such key words, the voice recognition system delivers an input to the processor through the interface board which input is equivalent to manual actuation of the suction button 123 and/or irrigation button 113 of the actuation mechanism 110 (e.g., suction-inducing section 122, irrigation-inducing section 112). The number of words that need to be recognized by the system is limited and thus does not require an extensive memory capacity for the stored vocabulary information. These stored words may include the names of the functions associated with controls; the words "start" and "finish" for providing select inputs; the words "reset" and "error" corresponding to respective controls on the user interface 150.

In a non-limiting exemplary embodiment, a numeric vocabulary may be provided, which is sufficient for recognition of the various input numbers representative of individual throw scores for providing input to the processor equivalent to actuation of the user interface 150. Various voice-activated mechanisms are now commercially available and have a sufficient vocabulary for use with the present disclosure. While many of the presently available voice-activated mechanisms need to be "trained" to recognize the sounds spoken by a particular individual and will not readily recognize the same words spoken by someone else, to an increasing extent newer systems being developed are more flexible in the range of voices to which the device will respond. For example, there are a number of voice recognitions systems that have of late become commercially available for use with personal computer systems. Such a voice-activated mechanism is capable of responding to a limited vocabulary carefully enunciated by a speaker without preliminary training of the system to the particular speaker's voice.

In a non-limiting exemplary embodiment, the voice-activated mechanism 151 may include a voice synthesized output system which is connected to an output port of the processor through the interface. The system is desirably provided with output selection switching means which allow users to select either a voice synthesized output, a numerical readout output through the displays, or simultaneous output through both the voice synthesizer and the panel displays. The panel displays have the advantage of continuity of output, in that information may be read at a glance by the users, while the voice output is stated once for each data update by the processor. Continuous repetition of the data by the voice synthesizer would be too annoying and would distract the user. It is contemplated, therefore, that the disclosure be provided with both visual and audible output systems. The voice output overcomes certain limitations of the panel readouts, but preferably does not replace the panel readouts.

To avoid interference between the voice output and voice inputs systems, the voice-activated mechanism 151 is disabled during output by the voice synthesizer.

In a preferred embodiment of the present disclosure, the voice synthesizer includes suitable audio amplifier means and acoustic driver such as a loudspeaker for delivering the voice output at a sufficient volume and low distortion to be clearly heard by all users.

In a further embodiment of the disclosure, the voice synthesizer output signal is connected for modulating a low power radio frequency signal. The radio frequency carrier modulated with the data is received by lightweight, portable miniaturized radio receives tuned to the transmitter frequency and accessed by each user. The personal receivers derive an audio output from the modulated signal for driving lightweight headphones for earphones worn by the user to assure clear communication of the score output information impedance by noise in the environment.

To increase the reliability of the voice recognition input system, the voice recognition system of the voice-activated mechanism 151 is normally nonresponsive to the various preprogrammed key words and is only responsive to a password which is preprogrammed in the system. Recognition of the password by the system opens a window in time, that is, a period of time during which the system becomes responsive to the key words. In this manner, the fluid displacing mechanism 103 and/or actuation mechanism 110 is not erroneously activated and confused by keyword spoken unintentionally during normal conversation between a user and a bystander. This period of time during which the voice recognition system becomes fully operative may be relatively brief, such as five seconds since typically only one or two words need to be spoken as the voice input.

The voice synthesizer output system can be readily constructed by a person skilled in the art based on any one of several commercially available electronic voice synthesis boards available from many suppliers and can be programmed to generate any desired vocabulary, limited only by the memory capacity of the particular system. The interfacing of such a voice synthesizer system to the processor through an interface will be apparent to those skilled in the art and is readily achievable using known design techniques.

In a non-limiting exemplary embodiment, the lavage handle 100 may further include a fluid-storage container 157 in communication with the power-operated fluid-displacing mechanism 103. As one option, a vacuum pump 129 is intermedially communicated with external suction tube 165 and first reservoir 148 for displacing fluid/debris upstream towards fluid-storage container 157, and a second reservoir 149 for displacing fluid downstream away from irrigation supply reservoir. As perhaps best shown in FIG. 14, such reservoirs 148, 149 may include at least one of an irrigation container 158 and a suction container 159 coupled to the body 101. Of course, such containers 158, 159 may be permanently affixed or detachably coupled to the body 101. The irrigation container 158 is isolated from the suction container 159 to prevent cross-contamination of the irrigated and collected fluids, for obvious reasons.

In a non-limiting exemplary embodiment, the first operating mode of the power-operated fluid-displacing mechanism 103 causes fluid displacement from the irrigation container 158 to the target zone 102.

In a non-limiting exemplary embodiment, the second operating mode of the power-operated fluid-displacing mechanism 103 causes fluid retrieval from the target zone 102 to the suction container 159.

In a non-limiting exemplary embodiment, the lavage handle 100 may further include a probe connector 140 in fluid communication with the body 101 to allow the user to connect, as desired, at least one of a suction probe 139 and an irrigation probe 139 in fluid communication with the probe connector 140.

In a non-limiting exemplary embodiment, the power-operated fluid-displacing mechanism 103 is at least partially contained within the body 101.

The present disclosure further includes a method of utilizing a lavage handle 100 for facilitating at least one of an irrigation function 175 (e.g., FIGS. 12A, 12B) and a suction function 174 (e.g., FIGS. 13A, 13B) at a target zone 102. Such method includes the steps of: providing a portable body 101; providing and communicating a power-operated fluid-displacing mechanism 103 with the body 101, the fluid-displacing mechanism 103 having one of a first operating mode (e.g., irrigation function 175) for inducing outward irrigation of fluid towards the target zone 102 and a second operating mode (e.g., suction function 174) for inducing inward suction of fluid from the target zone 102; providing and locating an actuation mechanism 110 at the body 101; and operably communicating the actuation mechanism 110 with the fluid-displacing mechanism 103 such that the fluid-displacing mechanism 103 is selectively operated in at least one of the first operating mode and the second operating mode.

In a non-limiting exemplary embodiment, the method further includes the steps of: accessing a target zone 102 during a surgical procedure; and employing the lavage handle 100 during the surgical procedure.

In a non-limiting exemplary embodiment, the method further includes the steps of: accessing a surgical port at the target zone 102; and employing the lavage handle 100 in conjunction with the surgical port.

In a non-limiting exemplary embodiment, the method further includes the steps of: obtaining at least one of a suction probe 139 and an irrigation probe 139; and employing the lavage handle 100 in conjunction with the at least one of a suction probe 139 and an irrigation probe 139.

Referring to FIGS. 20-20B, a non-limiting exemplary embodiment of the lavage handle 200 is illustrated wherein the body 201 is bifurcated into an upper section 291 and a lower section 292 detachably and operably coupled to the upper section 291. In this manner, a portion of the fluid-displacing mechanism 203, a portion of the actuation mechanism 210, a portion of the irrigation-inducing section 212, and a portion of the suction-inducing section 222 may be located at the upper section 291 and/or lower section 292 and, thereby substituted as desired. Such a bifurcated configuration enables a user to customize the lavage handle 200 by employing a variety of such above-referenced components as needed for the particular application.

In a non-limiting exemplary embodiment, the lower section 292 may be configured for performing at least one of the irrigation function 175 and suction function 174 wherein, after use, each of the upper section 291 and/or lower section 292 can be discarded or reused after proper sterilization.

In a non-limiting exemplary embodiment, the upper section 291 may be retrofitted to operably connect to a variety of lower sections 292 (which may be dedicated to one or more irrigation functions 175 and/or suction functions 174).

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A lavage handle for facilitating at least one of an irrigation function and a suctioning function at a target zone, said lavage handle comprising:
    a body;
    a fluid-displacing mechanism in communication with said body, said fluid-displacing mechanism having one of a first operating mode for inducing outward irrigation of fluid towards the target zone and a second operating mode for inducing inward suction of fluid from the target zone;
    an actuation mechanism located at said body and operably communicated with said fluid-displacing mechanism such that said fluid-displacing mechanism is selectively operated in at least one of said first operating mode and said second operating mode;
    a fluid storage container in communication with said fluid-displacing mechanism, said fluid storage container including at least one of an irrigation container and a suction container in communication with said body, said at least one of said irrigation container and said suction container being located external of said body;
    a probe connector in fluid communication with a distal end of said body, said probe connector including
        a probe connector port located exterior of said distal end of said body for providing an inlet and an outlet for the fluid-displacing mechanism, wherein said probe connector port has a single distal opening that diverges proximally away from said distal end of said body, said probe connector port having a threaded outer surface,
        a suction connector port in fluid communication with said probe connector port, and
        an irrigation connector port in fluid communication with said probe connector port;
    wherein said probe connector port proximally bifurcates into said suction connector port and said irrigation connector port;
    an internal suction tube connected to said suction connector port;
    an internal irrigation tube connected to said irrigation connector port;
    an external suction tube connector located at a proximal end of said body and connected to said internal suction tube;
    an external irrigation tube connector located at said proximal end of said body and connected to said internal irrigation tube; and
    at least one of a suction probe and an irrigation probe in fluid communication with said threaded outer surface of said probe connector.

2. The lavage handle of claim 1, wherein said actuation mechanism is disposed at least partially exterior of said body.

3. The lavage handle of claim 2, wherein said actuation mechanism comprises: a multi-pole toggle switch.

4. The lavage handle of claim 2, wherein said actuation mechanism comprises: at least one rheostat.

5. The lavage handle of claim 2, wherein said actuation mechanism comprises: a spring-resistive trigger.

6. The lavage handle of claim 1, wherein said actuation mechanism is disposed entirely interior of said body.

7. The lavage handle of claim 6, wherein said body is formed from deformably resilient material.

8. The lavage handle of claim 7, wherein said actuation mechanism comprises: a pressure-sensitive contact in communication with said deformably resilient material such that said fluid-displacing mechanism is operated when said body is biased to a tensioned state.

9. The lavage handle of claim 1, further comprising:
    a feedback mechanism in communication with said fluid-displacing mechanism for notifying a user of at least one of said first operating mode and said second operating mode.

10. The lavage handle of claim 9, wherein said feedback mechanism comprises: at least one transducer for generating and emitting at least one alert signal when said fluid-displacing mechanism is at one of said first operating mode and said second operating mode.

11. The lavage handle of claim 10, wherein said at least one alert signal is selected from the group comprising: an audio signal, a visual signal, a mechanical signal, a sensory signal and a combination thereof.

12. The lavage handle of claim 9, wherein said feedback mechanism is located interior of said body.

13. The lavage handle of claim 9, wherein said feedback mechanism is located at least partially exterior of said body.

14. A lavage handle for facilitating at least one of an irrigation function and a suctioning function at a target zone, said lavage handle comprising:
a portable body;
a power-operated fluid-displacing mechanism in communication with said body, said fluid-displacing mechanism having one of a first operating mode for inducing outward irrigation of fluid towards the target zone and a second operating mode for inducing inward suction of fluid from the target zone;
an actuation mechanism located at said body and operably communicated with said power-operated fluid-displacing mechanism such that said power-operated fluid-displacing mechanism is selectively operated in at least one of said first operating mode and said second operating mode; and
a fluid storage container in communication with said power-operated fluid-displacing mechanism, said fluid storage container including an irrigation container and a suction container each in communication with said body, said irrigation container and said suction container each being located external of said body;
a probe connector in fluid communication with a distal end of said body, said probe connector including
a probe connector port located exterior of said distal end of said body for providing an inlet and an outlet for the fluid-displacing mechanism, wherein said probe connector port has a single distal opening that diverges proximally away from said distal end of said body, said probe connector port having a threaded outer surface,
a suction connector port in fluid communication with said probe connector port, and
an irrigation connector port in fluid communication with said probe connector port;
wherein said probe connector port proximally bifurcates into said suction connector port and said irrigation connector port;
an internal suction tube connected to said suction connector port;
an internal irrigation tube connected to said irrigation connector port;
an external suction tube connector located at a proximal end of said body and connected to said internal suction tube;
an external irrigation tube connector located at said proximal end of said body and connected to said internal irrigation tube; and
at least one of a suction probe and an irrigation probe in fluid communication with said threaded outer surface of said probe connector.

15. The lavage handle of claim 14, further comprising:
a user-interface; and
a voice-activated mechanism operatively coupled to said actuation mechanism;
wherein, upon receiving a user input signal, said user-interface generates and transmits a corresponding control signal to said voice-activated mechanism for operating said actuation mechanism.

16. The lavage handle of claim 14, further comprising:
a flow monitoring mechanism in communication with said power-operated fluid-displacing mechanism, said flow monitoring mechanism monitoring at least one of a flow pressure, flow rate, and a volume of the fluid passing through said body.

17. The lavage handle of claim 14, further comprising:
an optics generating mechanism in communication with said body, said optics generating mechanism including at least one of a light source for illuminating the target zone and a camera for capturing a visual image of the target zone.

18. The lavage handle of claim 14, wherein said first operating mode of said power-operated fluid-displacing mechanism causes fluid displacement from said irrigation container to the target zone;
wherein said second operating mode of said power-operated fluid-displacing mechanism causes fluid retrieval from the target zone to said suction container.

19. The lavage handle of claim 14, wherein said power-operated fluid-displacing mechanism is at least partially contained within said body.

20. The lavage handle of claim 14, wherein said actuation mechanism comprises:
an irrigation-inducing mechanism.

21. The lavage handle of claim 14, wherein said actuation mechanism comprises: a suction-inducing mechanism.

22. A method of utilizing a lavage handle for facilitating at least one of an irrigation function and a suctioning function at a target zone, said method comprising the steps of:
providing a portable body;
providing and communicating a power-operated fluid-displacing mechanism with said body, said fluid-displacing mechanism having one of a first operating mode for inducing outward irrigation of fluid towards the target zone and a second operating mode for inducing inward suction of fluid from the target zone;
providing and locating an actuation mechanism at said body;
operably communicating said actuation mechanism with said fluid-displacing mechanism such that said fluid-displacing mechanism is selectively operated in at least one of said first operating mode and said second operating mode; and
providing and communicating a fluid storage container with said power-operated fluid-displacing mechanism, said fluid storage container including an irrigation container and a suction container each in communication with said body, said irrigation container and said suction container each being located external of said body;
a probe connector in fluid communication with a distal end of said body, said probe connector including
a probe connector port located exterior of said distal end of said body for providing an inlet and an outlet for the fluid-displacing mechanism, wherein said probe connector port has a single distal opening that diverges proximally away from said distal end of said body, said probe connector port having a threaded outer surface,
a suction connector port in fluid communication with said probe connector port, and
an irrigation connector port in fluid communication with said probe connector port;
wherein said probe connector port proximally bifurcates into said suction connector port and said irrigation connector port;
an internal suction tube connected to said suction connector port;
an internal irrigation tube connected to said irrigation connector port;

an external suction tube connector located at a proximal end of said body and connected to said internal suction tube;

an external irrigation tube connector located at said proximal end of said body and connected to said internal irrigation tube; and at least one of a suction probe and an irrigation probe in fluid communication with said threaded outer surface of said probe connector.

23. The method of claim 22, further comprising the steps of:

accessing a surgical procedure; and employing said lavage handle during said surgical procedure.

24. The method of claim 22, further comprising the steps of:

accessing a surgical port; and employing said lavage handle in conjunction with said surgical port.

25. The method of claim 22, further comprising the steps of:

obtaining at least one of a suction probe and an irrigation probe; and employing said lavage handle in conjunction with said at least one of a suction probe and an irrigation probe.

\* \* \* \* \*